(12) United States Patent
Matsumura et al.

(10) Patent No.: US 9,046,769 B2
(45) Date of Patent: Jun. 2, 2015

(54) PATTERN-FORMING METHOD, AND COMPOSITION FOR FORMING RESIST UNDERLAYER FILM

(71) Applicant: JSR Corporation, Tokyo (JP)

(72) Inventors: Yushi Matsumura, Tokyo (JP); Shinya Minegishi, Tokyo (JP); Satoru Murakami, Tokyo (JP); Yusuke Anno, Tokyo (JP); Shinya Nakafuji, Tokyo (JP); Kazuhiko Komura, Tokyo (JP); Kyoyu Yasuda, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 14/477,306

(22) Filed: Sep. 4, 2014

(65) Prior Publication Data

US 2014/0371466 A1    Dec. 18, 2014

Related U.S. Application Data

(63) Continuation of application No. 13/466,126, filed on May 8, 2012, now Pat. No. 8,859,191.

(30) Foreign Application Priority Data

May 11, 2011  (JP) .................................. 2011-106746
Apr. 23, 2012  (JP) .................................. 2012-098261

(51) Int. Cl.
*G03F 7/027* (2006.01)
*G03F 7/11* (2006.01)
*B44C 1/22* (2006.01)
*C07D 407/12* (2006.01)
*C07D 487/04* (2006.01)
*H05K 1/00* (2006.01)
*G03F 7/004* (2006.01)

(52) U.S. Cl.
CPC *G03F 7/027* (2013.01); *G03F 7/11* (2013.01); *B44C 1/22* (2013.01); *C07D 407/12* (2013.01); *C07D 487/04* (2013.01); *H05K 1/00* (2013.01); *G03F 7/004* (2013.01)

(58) Field of Classification Search
CPC .... C07D 407/12; C07D 487/04; G03F 7/027; G03F 7/11; G03F 7/004
USPC ..................... 430/270.1; 548/303.4; 549/557
See application file for complete search history.

(56) References Cited

U.S. PATENT DOCUMENTS

| | | | |
|---|---|---|---|
| 8,513,133 B2 | 8/2013 | Minegishi et al. | |
| 8,859,185 B2 | 10/2014 | Minegishi et al. | |
| 2005/0282091 A1 | 12/2005 | Hatakeyama | |
| 2007/0154837 A1 | 7/2007 | Lee et al. | |
| 2012/0129108 A1* | 5/2012 | Aqad et al. .................... | 430/325 |
| 2012/0270157 A1 | 10/2012 | Minegishi et al. | |

FOREIGN PATENT DOCUMENTS

| | | |
|---|---|---|
| JP | 10-092740 | 4/1998 |
| JP | 2002-296789 | 10/2002 |
| JP | 2004-168748 | 6/2004 |
| JP | 2004-177668 | 6/2004 |

* cited by examiner

*Primary Examiner* — Brittany Raymond
(74) *Attorney, Agent, or Firm* — Oblon, McClelland, Maier & Neustadt, L.L.P.

(57) ABSTRACT

Providing a method for forming a pattern capable of forming a resist underlayer film that can be easily removed using an alkali liquid while maintaining etching resistance is objected to. Provided by the present invention is a method for forming a pattern, the method including: (1) forming a resist underlayer film on a substrate using a composition for forming a resist underlayer film containing a compound having an alkali-cleavable functional group; (2) forming a resist pattern on the resist underlayer film; (3) forming a pattern on the substrate by dry etching of the resist underlayer film and the substrate, using the resist pattern as a mask; and (4) removing the resist underlayer film with an alkali liquid.

11 Claims, No Drawings

PATTERN-FORMING METHOD, AND COMPOSITION FOR FORMING RESIST UNDERLAYER FILM

This application is a Continuation of U.S. application Ser. No. 13/466,126, filed on May 8, 2012, now allowed.

BACKGROUND OF THE INVENTION

1. Field of Invention

The present invention relates to a method for forming a pattern, and a composition for forming a resist underlayer film.

2. Description of the Related Art

In producing elements of integrated circuits, a multilayer resist process has been employed nowadays in order to achieve a higher degree of integration. In brief, according to this process, a composition for a resist underlayer film is first coated on a substrate to be processed (hereinafter, merely referred to as "substrate"), thereby forming a resist underlayer film, on which a resist composition is coated to form a resist coating film, followed by transferring a mask pattern using a reduced projection exposure system (stepper), and developing with an appropriate developer to obtain a resist pattern. Subsequently, the resist pattern is transferred to the resist underlayer film by dry etching, and further the resist underlayer film pattern is transferred to the substrate by dry etching to enable a substrate having a desired pattern formed to be obtained.

In such a multilayer resist process, it is necessary to remove an underlayer film pattern remaining on the substrate, and for this purpose, a method including an ashing treatment by oxygen plasma or the like has been commonly employed (see Japanese Unexamined Patent Application, Publication No. H10-92740). However, when such an ashing treatment is carried out, disadvantages may occur such as deterioration of the surface of the substrate such as silicon, or increase in the relative permittivity in the case of substrate materials having a low relative permittivity, and the like.

In order to eliminate the foregoing disadvantages, a method for removing an underlayer film pattern in which an ashing treatment is not carried out has been desired. As such a type of method, for example, an underlayer film form material has been proposed which contains a resin component having a substituent that generates a sulfonate group upon application of a predetermined energy to remove a terminal group (see Japanese Unexamined Patent Application, Publication No. 2004-177668). According to this technique, sulfonate groups are generated on the underlayer film resin by applying the energy such as heating in forming the resist underlayer film; therefore, removal with a removing liquid after the dry etching can be carried out, whereby the necessity of the ashing treatment is obviated. However, in this case, it is necessary to elevate the temperature to 80° C. or higher during the resist underlayer film is formed, and a strong acid group that is a sulfonate group continuously exerts influences on the substrate during the dry etching; therefore, occurrence of deterioration of the surface of the substrate, and the like has not yet been overcome.

PRIOR ART DOCUMENTS

Patent Documents

Patent Document 1: Japanese Unexamined Patent Application, Publication No. H10-92740

Patent Document 2: Japanese Unexamined Patent Application, Publication No. 2004-177668

SUMMARY OF THE INVENTION

The present invention was made in view of these disadvantages, and an object of the invention is to provide a method for forming a pattern, which enables a resist underlayer film to be easily removed using an alkali liquid, while maintaining the etching resistance of the resist underlayer film formed; and a composition for forming a resist underlayer film suitably used for the method for forming a pattern.

An aspect of the present invention which was made for solving the foregoing problems is a method for forming a pattern, the method comprising the steps of:

(1) forming a resist underlayer film on a substrate (i.e., substrate to be processed) using a composition for forming a resist underlayer film (hereinafter, may be also referred to as "composition (A) for forming a resist underlayer film") containing a compound having an alkali-cleavable functional group (hereinafter, may be also referred to as "compound (A)");

(2) forming a resist pattern on the resist underlayer film;

(3) forming a pattern on the substrate by dry etching of the resist underlayer film and the substrate, using the resist pattern as a mask; and (4) removing the resist underlayer film with an alkali liquid.

According to the method for forming a pattern of the present invention, by using a composition for forming a resist underlayer film containing a compound (A) having an alkali-cleavable functional group, the resist underlayer film formed from the composition maintains etching resistance, and the alkali-cleavable functional group produces a polar group by cleavage with an alkali liquid to make the resist underlayer film soluble in an alkali liquid, thereby enabling the resist underlayer film to be easily removed, and as a result, a pattern can be conveniently formed. In addition, according to the method for forming a pattern, it is believed that since the resist underlayer film pattern remaining on the substrate after the dry etching can be removed without an ashing treatment, and without need of application of energy by e.g., heating at a high temperature, a pattern having favorable qualities can be formed without influences such as deterioration, on the substrate having a pattern formed thereon.

In the method for forming a pattern, the compound having an alkali-cleavable functional group in the composition for forming a resist underlayer film preferably has crosslinkability. In the method for forming a pattern, since the compound (A) is a crosslinkable compound, a resist underlayer film that is superior in strength and has high etching resistance can be formed by a crosslinking reaction, whereby more convenient pattern formation is enabled.

In the method for forming a pattern, the compound having an alkali-cleavable functional group is preferably represented by the following formula (1):

[chemical formula 1]

(1)

in the formula (1), $Y^1$ and $Y^2$ each independently represent a crosslinkable functional group; X represents an alkali-cleavable functional group; $R^1$ represents a linking group having a valency of (n1+1); $R^2$ represents a linking group having a valency of (n2+m); n1 is an integer of 1 to 3; n2 is an integer of 0 to 3; m is an integer of 1 to 3; wherein, n1, m and n2 satisfy the formula of: (n1×m+n2)≥2, and provided that $Y^1$, $Y^2$, X or $R^1$ is each present in plural number, the $Y^1$, $Y^2$, X or $R^1$ present in plural number may be each the same or different.

According to the method for forming a pattern, since the compound (A) in the composition for forming a resist underlayer film has the specific structure described above, a crosslinking bond can be effectively cleaved with an alkali liquid in the resist underlayer film formed by crosslinking with this compound. Therefore, the resist underlayer film can be more easily removed, and thus more convenient formation of the pattern is enabled.

In the method for forming a pattern, the compound represented by the above formula (1) is preferably represented by the following formula (1-1) or (1-2):

[chemical formula 2]

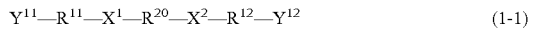  (1-1)

$Y^{11}-R^{11}-X^1-R^{20}-X^2-R^{12}-Y^{12}$ (1-1)

[chemical formula 3]

$Y^{2'}-R^{20'}-X'-R^{1'}-Y^{1'}$ (1-2)

in the formulae (1-1) and (1-2), $Y^{11}$, $Y^{12}$, $Y^{1'}$ and $Y^{2'}$ each independently represent a monovalent group each represented by the following formulae (Y1) to (Y4):

[chemical formula 4]

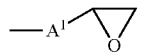 (Y1)

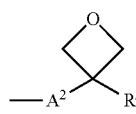 (Y2)

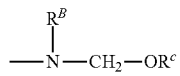 (Y3)

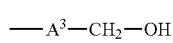 (Y4)

(in the formulae (Y1) to (Y4), $A^1$ and $A^2$ each independently represent a single bond, an alkanediyl group having 1 to 4 carbon atoms or an oxyalkanediyl group; $A^3$ represents a bivalent aromatic hydrocarbon group; $R^A$ represents an alkyl group having 1 to 4 carbon atoms; $R^B$ represents a hydrogen atom or an alkyl group having 1 to 6 carbon atoms; and $R^C$ represents an alkyl group having 1 to 4 carbon atoms); $X^1$, $X^2$ and X' represent an ester group; $R^{11}$, $R^{12}$, $R^{1'}$, $R^{20}$ and $R^{20'}$ each independently represent a phenylene group, a naphthylene group, an isopropylidenediphenylene group or an alkanediyl group having 1 to 6 carbon atoms which is unsubstituted or substituted with a fluorine atom, wherein a part or all of hydrogen atoms of the aromatic ring of the phenylene group, the naphthylene group and the isopropylidenediphenylene group are unsubstituted or substituted by an alkyl group, a cycloalkyl group, an aryl group, a halogen atom, a hydroxyl group, a cyano group or an amino group.

According to the method for forming a pattern, due to having the aforementioned specific structure and crosslinkable functional group, the compound (A) in the composition for forming a resist underlayer film enables a resist underlayer film to be formed which has more superior strength and etching resistance, and can be more easily removed with an alkali liquid, whereby still more convenient pattern formation is enabled.

In the method for forming a pattern, it is also preferred that the compound having an alkali-cleavable functional group in the composition for forming a resist underlayer film be a polymer. According to the method for forming a pattern, due to the compound (A) being a polymer, a resist underlayer film that is superior in strength and has higher etching resistance can be formed.

In the method for forming a pattern, the polymer preferably has (P) a structure unit that includes an aromatic group or an alicyclic group. According to the method for forming a pattern, since the polymer has the structure unit (P), the content of carbon in the resist underlayer film formed can be increased, and as a result, etching resistance in pattern formation can be further enhanced.

In the method for forming a pattern, as the structure unit (P) of the polymer a structure unit derived from at least one hydrocarbon selected from the group consisting of acenaphthylene, naphthalene, fluorene, indene and nortricyclene is preferably included. According to the method for forming a pattern, since the structure unit (P) is derived from the aforementioned specific hydrocarbon, the content of carbon in the resist underlayer film formed can be further increased, and as a result, etching resistance in pattern formation can be further enhanced.

Characteristic features of the composition for forming a resist underlayer film according to an aspect of the present invention include: being a composition for forming a resist underlayer film for use in a method for forming a pattern in which the resist underlayer film is removed using an alkali liquid; and containing a compound having an alkali-cleavable functional group. According to the composition for forming a resist underlayer film, due to containing a compound having an alkali-cleavable functional group, the resist underlayer film that can be more easily removed with an alkali liquid can be formed while maintaining the etching resistance. As a result, according to the composition for forming a resist underlayer film, it is believed that simplification of pattern formation is enabled, and the resist underlayer film pattern remaining on the substrate after the dry etching can be removed without an ashing treatment, and without need of application of energy by e.g., heating at a high temperature, a pattern having favorable qualities can be formed without influences such as deterioration, on the substrate having a pattern formed thereon.

As explained in the foregoing, according to the method for forming a pattern, and the composition for forming a resist underlayer film of the present invention, the resist underlayer film can be more easily removed with an alkali liquid while maintaining the etching resistance of the resist underlayer film formed, whereby a pattern can be conveniently formed.

DESCRIPTION OF EMBODIMENTS

<Method for Forming a Pattern>

The method for forming a pattern of the present invention includes the steps of:

(1) forming a resist underlayer film on a substrate using a composition for forming a resist underlayer film containing a compound having an alkali-cleavable functional group (hereinafter, may be also referred to as "step (1)"), (2) forming a resist pattern on the resist underlayer film (hereinafter, may be also referred to as "step (2)"), (3) forming a pattern on the substrate by dry etching of the resist underlayer film and the substrate with the resist pattern as a mask (hereinafter, may be also referred to as "step (3)"), and (4) removing the resist underlayer film with an alkali liquid (hereinafter, may be also referred to as "step (4)").

According to the method for forming a pattern, by using a composition for forming a resist underlayer film containing a compound (A) having an alkali-cleavable functional group, the resist underlayer film formed from the composition maintains etching resistance, and the alkali-cleavable functional group produces a polar group by cleavage with an alkali liquid to make the resist underlayer film soluble in an alkali liquid, thereby enabling the resist underlayer film to be easily removed. As a result, a pattern can be conveniently formed according to the method for forming a pattern.

In addition, according to the method for forming a pattern, it is believed that the resist underlayer film pattern remaining on the substrate after the dry etching can be removed without an ashing treatment, and without need of application of energy by e.g., heating at a high temperature, a pattern having favorable qualities can be formed without influences such as deterioration, on the substrate having a pattern formed thereon. Hereinafter, each step is explained.

[Step (1)]

In the step (1), a resist underlayer film is formed on a substrate using the composition (A) for forming a resist underlayer film. In this step, after forming a coating film by coating the composition (A) for forming a resist underlayer film on the substrate, in general, the resist underlayer film is formed by heating the coating film.

As the substrate, for example, a silicon wafer, a wafer covered with aluminum, or the like may be used. Also, the coating method for coating the composition for forming a resist underlayer film onto the substrate is not particularly limited, but an appropriate method such as spin coating, cast coating or roll coating may be employed.

After forming the coating film, in general, the resist underlayer film is formed on the substrate by heating the resultant coating film and the substrate. Accordingly, a substrate provided with a resist underlayer film can be obtained in which a resist underlayer film is formed on a substrate. The resist underlayer film formed in this step (1) has a film thickness of usually 0.05 μm to 5 μm.

The coating film and substrate is generally heated in ambient air. The heating temperature is usually 200° C. to 400° C., and preferably 200° C. to 300° C. When the heating temperature is less than 200° C., oxidative crosslinking does not sufficiently proceed, whereby performances of the resist underlayer film obtained may be deteriorated. The heating time is 30 sec to 1,200 sec, and preferably 60 sec to 600 sec.

The oxygen concentration during heating the coating film and the substrate is suitably no less than 5% by volume. When the oxygen concentration during heating is low, the oxidative crosslinking of the underlayer film does not sufficiently proceed, whereby performances of the underlayer film obtained may be deteriorated.

Prior to heating the coating film and substrate at a temperature of 200° C. to 400° C., it may be preheated at a temperature of 60 to 200° C. The heating time in the preheating is not particularly limited, and is preferably 10 to 300 sec, and more preferably 30 to 180 sec. The preheating causes the solvent to vaporize beforehand and makes the film become compact, whereby the dehydrogenation reaction can efficiently proceed.

In the step (1), the coating film is usually hardened by heating the coating film to form a resist underlayer film. However, it is also possible to form the resist underlayer film by adding a certain photocuring agent (crosslinking agent) to the composition for forming a resist underlayer film, and permitting photocuring by subjecting to an exposing process of the heated coating film. The type of radioactive ray used for the exposure is appropriately selected according to the type of the acid generating agent added to the resin composition for forming a resist underlayer film from among visible rays, ultraviolet rays, far ultraviolet rays, X-rays, electron beams, γ-rays, molecular beams, ion beams, and the like.

Also, the method for forming a pattern may further include a step of forming an intermediate layer (intermediate coating film) after the step (1) as needed. The intermediate layer is a layer for reinforcing the functions possessed by the resist underlayer film and/or the resist coating film or for providing functions with the resist underlayer film and/or the resist film which are not possessed by these films, in forming a resist pattern. In the case in which an antireflective film is, for instance, formed as the intermediate layer, the intermediate film can reinforce the antireflecting function of the resist underlayer film.

The intermediate layer may be formed from an organic compound or an inorganic oxide. Examples of the organic compound include materials commercially available under the trade names of "DUV-42", "DUV-44", "ARC-28", "ARC-29" and the like manufactured by Brewer Science, Inc., and "AR-3", "AR-19" and the like manufactured by Lohm and Haas Company, and the like. Examples of the inorganic oxide include polysiloxane, titanium oxide, alumina, tungsten oxide, and the like.

The method of forming the intermediate layer is not particularly limited, but for example, a coating method, a CVD method or the like can be employed. Of these, the coating method is preferred. When the coating method is employed, the intermediate layer may be consecutively formed after forming the resist underlayer film.

The film thickness of the intermediate layer is not particularly limited, and may be appropriately selected according to functions demanded for the intermediate layer but falls within the range of preferably 10 to 3,000 nm, and more preferably 20 to 300 nm.

[Step (2)]

In the step (2), a resist pattern is formed on the resist underlayer film. The method of forming a resist pattern in the step (2) may be exemplified by (2A) a method in which a resist composition is used, (2B) a method in which a nanoimprint lithography technique is employed, (2C) a method in which a directed self-assembly composition is used, and the like.

[(2a) Method in which a Resist Composition is Used]

When carried out using a resist composition (2A), the step (2) may include, for example, (2-A1) a step of forming a resist coating film on the resist underlayer film using a resist composition (hereinafter, may be also referred to as "step (2-A1)");

(2-A2) a step of exposing the resist coating film by irradiating with exposure light through a photomask (hereinafter, may be also referred to as "step (2-A2)"); and (2-A3) a step of forming a resist pattern by development of the exposed resist coating film (hereinafter, may be also referred to as "step (2-A3)").

(Step (2-A1))

In the step (2-A1), a resist coating film is formed on the resist underlayer film using a resist composition. Specifically, after coating the resist composition such that the resultant resist coating film has a predetermined film thickness, the solvent in the coating film is volatilized by prebaking to form the resist coating film.

Examples of the resist composition include, a positive type or negative type chemically amplified resist composition containing a photoacid generating agent, a positive type resist composition including an alkali-soluble resin and a quinondiazide-based sensitizer, a negative type resist composition including an alkali-soluble resin and a crosslinking agent, and the like.

The resist composition for use in forming the resist coating film on the resist underlayer film may have a solid content of usually about 5 to 50% by mass, and in general, the resist composition is subjected to formation of the resist coating film after filtering through a filter with a pore size of about 0.2 μm, for example. It is to be noted that a commercially available resist composition may be used as is in this step.

The coating method of the resist composition is not particularly limited, and for example, a spin coating method or the like may be performed. In addition, the temperature of the prebaking may be appropriately adjusted according to the type and the like of the resist composition solution used, but is usually about 30 to 200° C., and preferably 50 to 150° C.

(Step (2-A2))

In the step (2-A2), the resist coating film formed in the step (2-A1) is exposed by irradiating with exposure light through a photomask. The exposure light for use in exposure is appropriately selected according to the type of the photoacid generating agent used in the resist composition from among visible rays, ultraviolet rays, far ultraviolet rays, X-rays, electron beams, γ-rays, molecular beams, ion beams, and the like. Of these, far ultraviolet rays are preferred, a KrF excimer laser beam (wavelength: 248 nm), an ArF excimer laser beam (wavelength: 193 nm), a $F_2$ excimer laser beam (wavelength: 157 nm), a $Kr_2$ excimer laser beam (wavelength: 147 nm), an ArKr excimer laser beam (wavelength: 134 nm) and extreme ultraviolet rays (wavelength: 13 nm, etc.) are more preferred, and an ArF excimer laser beam is still more preferred.

(Step (2-A3))

In the step (2-A3), the resist pattern is formed by development of the resist coating film exposed in the step (2-A2). The developer used in this step is appropriately selected according to the type of the resist composition. Specific examples include alkaline aqueous solutions of sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethyl ethanolamine, triethanolamine, tetramethylammonium hydroxide, tetraethylammonium hydroxide, pyrrole, piperidine, choline, 1,8-diazabicyclo[5.4.0]-7-undecene, 1,5-diazabicyclo[4.3.0]-5-nonene or the like. An appropriate amount of a water-soluble organic solvent, for example, an alcohol such as methanol or ethanol, and a surfactant may be optionally added to the alkaline aqueous solution.

The resist film after developing with the aforementioned developer is washed and dried to form a predetermined resist pattern. It is to be noted that in the step (2-2A), post-baking may be carried out after the exposure and before the development in order to improve the resolution, pattern profile, developability, and the like. The temperature of the post-baking is appropriately adjusted according to the type and the like of the resist composition used and is usually about 50 to 200° C., and preferably 70 to 150° C.

[(2B) Method in which a Nanoimprint Lithography Technique is Employed]

When carried out with a nanoimprint lithography technique (2B), the step (2) may include, for example, (2-B1) a step of forming a resist underlayer film on the pattern formation layer using a curable composition (hereinafter, may be also referred to as "step (2-B1)");

(2-B2) a step of bringing a surface of a mold having a reversal pattern into close contact with the pattern formation layer (hereinafter, may be also referred to as "step (2-B2)");

(2-B3) a step of exposing or heating the pattern formation layer while the mold is brought into contact (hereinafter, may be also referred to as "step (2-B3)"); and (2-B4) a step of forming a resist pattern by detaching from the exposed or heated pattern formation layer of the mold (hereinafter, may be also referred to as "step (2-B4)").

(Step (2-B1))

In the step (2-B1), the pattern formation layer is formed on the resist underlayer film using a curable composition. The curable composition is exemplified by a composition containing a polymerizable monomer or a polymerizable oligomer, and examples include radiation-sensitive curable compositions, thermosetting curable compositions, and the like. The curable composition may contain a curing accelerator and the like. Examples of the curing accelerator include radiation-sensitive curing accelerators such as a photoacid generating agent, a photobase generating agent, and a photosensitizer; thermal curing accelerators such as a thermal acid generating agent and a thermal base generating agent, and the like. The curing accelerators may be used in combination of two or more thereof.

The method of coating the curable composition is not particularly limited, and for example, an ink jet method, a dip coating method, an air knife coating method, a curtain coating method, a wire bar coating method, a gravure coating method, an extrusion coating method, a spin coating method, a slit scanning method, and the like.

(Step (2-B2))

In the step (2-B2), a surface of a mold having a reversal pattern is brought into close contact with the pattern formation layer. The surface of the mold has a reversal pattern of the shape of the resist pattern to be formed. Examples of the material of the mold include glass, quartz, optically transparent resins such as PMMA and polycarbonate; transparent metal vapor deposition films; soft films of polydimethyl siloxane or the like; photocured films; metal films, and the like. When a radiation-sensitive curable composition is used as the curable composition, a material that transmits radioactive rays is used as a mold.

The pressure applied when the mold is brought into close contact is usually 0.1 MPa to 100 MPa, preferably 0.1 MPa to 50 MPa, and more preferably 0.1 MPa to 30 MPa. The time period of bringing into close contact is usually 1 sec to 600 sec, preferably 1 sec to 300 sec, and more preferably 1 sec to 180 sec.

It is to be noted that the surface of the mold is preferably subjected to a hydrophobilization treatment using a release agent or the like prior to bringing into close contact. Examples of the release agent include silicon based release agents, fluorine based release agents, polyethylene based release agents, polypropylene based release agents, paraffin based release agents, montan based release agents, carnauba based release agents, and the like. It is to be note that the release agent may be used either alone, or two or more thereof may be used in combination. Among these, silicon based release agents are preferred. Examples of the silicon based release agent include polydimethyl siloxane, acrylsilicone graft polymer, acrylsiloxane, arylsiloxane, and the like.

(Step (2-B3))

In the step (2-B3), the pattern formation layer is exposed or heated while the mold is brought into contact. When a radiation-sensitive curable composition is used as the curable composition, exposure is carried out, whereas when a thermosetting composition is used, heating is carried out. Conditions of the exposure and heating may be appropriately selected according to the formulation of the curable composition used.

(Step (2-B4))

In the step (2-B4), a resist pattern is formed by detaching from the exposed or heated pattern formation layer of the mold. The method of the detachment is not particularly limited, and for example, it may be detached by: moving the mold while the pattern formation layer is fixed; moving the pattern formation layer while the mold is fixed; or moving both the mold and the pattern formation layer in the opposite direction.

[(2C) Method in which a Directed Self-Assembly Composition is Used]

When carried out using a directed self-assembly composition (2C), the step (2) may include, for example, (2-C1) a step of forming directed self-assembly film having a phase separation structure on the resist underlayer film using a directed self-assembly composition for pattern formation (hereinafter, may be also referred to as "step (2-C1)"), and (2-C2) a step of forming a resist pattern by removing a part of the phase of the directed self-assembly film (hereinafter, may be also referred to as "step (2-C2)").

(Step (2-C1))

In the step (2-C1), a directed self-assembly film having a phase separation structure is formed on the resist underlayer film using a directed self-assembly composition for pattern formation. Exemplary method of carrying out this step may include e.g., a method in which annealing or the like is conducted after coating a directed self-assembly composition for pattern formation, and the like.

The directed self-assembly composition for pattern formation is a composition for forming a phase separation structure by way of directed self-assembly. The directed self-assembly composition for pattern formation is exemplified by a composition containing a block copolymer, a composition containing at least two types of polymer, and the like. Specific examples of the directed self-assembly composition include compositions containing a block copolymer including a polystyrene block-polymethyl methacrylate block, compositions containing polystyrene and polymethyl methacrylate, and the like.

The method of coating the directed self-assembly composition for pattern formation on the resist underlayer film may include, for example, a spin coating method, and the like.

The annealing temperature is usually 80° C. to 400° C. The annealing time is usually 30 sec to 120 min.

It is to be noted that in order to attain more desirable phase separation structure to be obtained, a prepattern substantially perpendicular to the resist underlayer film, and/or other underlayer film laminated on the resist underlayer film are/is preferably formed prior to coating the directed self-assembly composition for pattern formation on the resist underlayer film.

(Step (2-C2))

In the step (2-C2), a resist pattern is formed by removing a part of the phase of the directed self-assembly film.

Exemplary method of removing a part of the phase of the directed self-assembly film may involve e.g., dry etching such as chemical dry etching, sputter etching, and ion beam etching; wet etching carried out using an etching liquid such as an organic solvent or hydrofluoric acid, and the like.

As the method of carrying out the step (2), the method in which a resist composition is used (2A) is preferable among the foregoings.

[Step (3)]

In the step (3), a pattern is formed on the substrate by dry etching of the resist underlayer film and the substrate, using the resist pattern formed in the step (2) as a mask.

The dry etching may be carried out with a well-known dry etching apparatus. Also, as a source gas for use during the dry etching, gas containing an oxygen atom such as $O_2$, CO or $CO_2$, inert gas such as He, $N_2$ or Ar, chlorine based gas such as $Cl_2$ or $BCl_3$, fluorine based gas such as $CHF_3$ or $CF_4$, or gas such as $H_2$ or $NH_3$ may be used although it may depend on the elemental composition of the object to be etched. It should be noted that the gas may be also used as a mixture.

[Step (4)]

In step (4), the resist underlayer film on a pattern-formed substrate is removed with an alkali liquid. The alkali liquid for use in the removal is not particularly limited as long as it is an alkaline liquid, and for example, alkaline aqueous solutions similar to those exemplified as a developer for use in the step (2-A3), and the like may be suitably used. Of these, alkaline aqueous solutions of sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethyl ethanolamine, triethanolamine, tetramethylammonium hydroxide, tetraethylammonium hydroxide, pyrrole, piperidine, choline, 1,8-diazabicyclo[5.4.0]-7-undecene, 1,5-diazabicyclo[4.3.0]-5-nonene or the like are preferred, and in light of availability, an alkaline aqueous solution of tetramethylammonium hydroxide is particularly preferred. An appropriate amount of a water-soluble organic solvent, for example, an alcohol such as methanol or ethanol, and a surfactant may be optionally added to the alkaline aqueous solution.

The concentration of the alkaline aqueous solution may be appropriately selected according to the type of the alkaline substance dissolved, it is usually 1% by mass to 20% by mass, preferably 2% by mass to 17% by mass, and more preferably 3% by mass to 15% by mass.

The temperature of the alkali liquid used is usually 5° C. to 75° C., preferably 20° C. to 70° C., and more preferably 30° C. to 60° C.

Although the method of bringing the alkali liquid into contact with the underlayer film pattern is not particularly limited, for example, a method of coating or spraying the alkali liquid, a method of immersing into the alkali liquid, and the like may be involved. Among these, the method of immersion is preferred in light of possibility of easier removal of the underlayer film pattern.

After the operation of removal with the alkali liquid, the substrate is preferably washed with an organic solvent or water in order to remove residues of the underlayer film pattern remaining on the substrate. The solvent employed is preferably an organic solvent, and in light of the solubility of the residues of the remaining underlayer film pattern, the solvent is preferably an alcoholic solvent, a ketone based solvent, and an ester based solvent, more preferably an alcoholic solvent, and particularly preferably 2-propanol.

<Composition for Forming a Resist Underlayer Film>

The composition for forming a resist underlayer film used in the present invention contains (A) a compound having an alkali-cleavable functional group. Furthermore, as suitable optional components, (B) a polymer not having an alkali-cleavable functional group (hereinafter, may be also referred to as merely "polymer (B)"), (C) an organic solvent, (D) an acid generator and (E) a crosslinkable compound other than the compound (A) (hereinafter, may be also referred to as "crosslinkable compound (E)") may be contained, and further other optional component may be also contained in the range not to impair the effects of the invention. Hereinafter, each constitutional component is explained in sequence.

<(A) Compound>

The compound (A) used in the present invention has an alkali-cleavable functional group. The compound (A) is not particularly limited as long as it has an alkali-cleavable functional group. The alkali-cleavable functional group as referred to herein means a group that generates a polar group such as a carboxyl group, a hydroxyl group or a sulfonate group upon cleavage in the presence of an alkali liquid (for example, in an aqueous tetramethylammonium hydroxide solution). The polar group generated upon cleavage of the alkali-cleavable functional group is preferably a carboxyl group and a phenolic hydroxyl group in light of high solubilities in alkali liquids, and small influences on the substrate due to lower acid strength.

The alkali-cleavable functional group is not particularly limited as long as it has the properties described above. Specific examples of the alkali-cleavable functional group include an ester group (—C(O)—O—), an acid anhydride group (—C(O)—O—(O)C—), a carbonate group (—O—C(O)—O—), a sulfonyloxy group (—S(O)$_2$—O—), and an oxime sulfonate group (—S(O)$_2$—O—N=C(R$^a$)R$^b$— (wherein, R$^a$ represents a monovalent organic group), and the like. Of these, in light of ease in cleavage, an ester group, an acid anhydride group and a carbonate group are preferred, and an ester group is more preferred.

The structure that binds to the alkali-cleavable functional group is not particularly limited as long as it has the aforementioned properties. However, in light of higher cleavability with alkali, and more facilitated removal of the resist underlayer film, the structure that binds to an oxygen atom such as a ester group, a carbonate group or a sulfonyloxy group is preferably an aromatic ring structure, an imide ring structure, a methyl structure to which an aromatic ring or an imide ring has been bound, or a methyl or ethyl structure to which a fluorine atom has been bound.

Also, the structure that binds to a carbonyl carbon atom of an ester group, an acid anhydride group, etc., and a sulfur atom of a sulfonyloxy group, an oxime sulfonate group, etc. is preferably a methyl structure to which an aromatic ring structure or a fluorine atom has been bound.

The position of the alkali-cleavable functional group in the compound (A) is not particularly limited, and may be included in the main skeleton chain that forms the compound (A), or may be included in the side chain bound to the main skeleton chain. Also, the number of alkali-cleavable functional groups included in the compound (A) is not particularly limited.

The compound (A) is preferably a compound having crosslinkability (hereinafter, may be also referred to as "crosslinkable compound (A1)"). Alternatively, it is also preferred that the compound (A) be a polymer (hereinafter, may be also referred to as "polymer (A2)"). Hereinafter, the crosslinkable compound (A1), and the polymer (A2) are explained in this order.

<(A1) Crosslinkable Compound>

The crosslinkable compound (A1) is a crosslinkable compound which has an alkali-cleavable functional group. The compound having crosslinkability is a compound having at least two crosslinkable functional groups, and these crosslinkable functional groups react to form a compound having a higher molecular weight between the crosslinkable compounds with each other, or between the crosslinkable compound and other compound. The number of the crosslinkable functional group in the crosslinkable compound (A1) is not particularly limited as long as the number of two or more.

The crosslinkable functional group is a functional group that can form a cross-linked structure by a chemical bond. Examples of the crosslinkable functional group include those each having an epoxy group, an oxetanyl group, an alkoxymethyl group, a hydroxyl group, an amino group, a silyl group, an alkenyl group, an isocyanate group, an aldehyde group, a cyano group, an isothiocyanate group, an acetoxymethyl group, a benzoyloxymethyl group, a formyl group, or an acetyl group. Of these, the crosslinkable functional each having an epoxy group, an oxetanyl group, an alkoxymethyl group, a hydroxyl group, a silyl group, an alkenyl group or an isocyanate group is preferred.

Examples of particularly preferable crosslinkable functional group include groups represented by the above formula (Y1) as the crosslinkable functional group having an epoxy group, groups represented by the above formula (Y2) as the crosslinkable functional group having an oxetanyl group, groups represented by the above formula (Y3) as the crosslinkable functional group having an alkoxymethyl group, and groups represented by the above formula (Y4) as the crosslinkable functional group having a hydroxyl group, respectively.

In the above formulae (Y1) to (Y4), $A^1$ and $A^2$ each independently represent a single bond, an alkanediyl group having 1 to 4 carbon atoms or an oxyalkanediyl group; $A^3$ represents a bivalent aromatic hydrocarbon group; $R^A$ represents an alkyl group having 1 to 4 carbon atoms; $R^B$ represents a hydrogen atom or an alkyl group having 1 to 6 carbon atoms; and $R^C$ represents an alkyl group having 1 to 4 carbon atoms.

Examples of the alkanediyl group having 1 to 4 carbon atoms represented by the $A^1$ and $A^2$ include a methanediyl group, a 1,1-ethanediyl group, a 1,2-ethanediyl group, a 1,1-propanediyl group, a 1,2-propanediyl group, a 1,3-propanediyl group, a 1,1-butanediyl group, a 1,2-butanediyl group, a 1,3-butanediyl group, a 1,4-butanediyl group, a 2,2-butanediyl group, a 2,3-butanediyl group, and the like. Of these, in light of increase of the rigidity and the carbon content of the cross-linked polymer formed from the crosslinkable compound (A), and enhancement of the strength and the etching resistance of the resultant resist underlayer film, a methanediyl group and a 1,1-ethanediyl group are preferred, and a methanediyl group is particularly preferred.

The oxyalkanediyl group having 1 to 4 carbon atoms represented by the $A^1$ and $A^2$ is preferably an oxymethanediyl group, an oxy-1,1-ethanediyl group, an oxy-1,2-ethanediyl group, an oxy-1,1-propanediyl group, an oxy-1,2-propanediyl group, an oxy-1,3-propanediyl group, an oxy-1,1-butanediyl group, an oxy-1,2-butanediyl group, an oxy-1,3-butanediyl group, an oxy-1,4-butanediyl group, an oxy-2,2-butanediyl group, an oxy-2,3-butanediyl group, and the like. Of these, an oxymethanediyl group and an oxy-1,1-ethanediyl group are preferred, and an oxymethanediyl group is particularly preferred. Of these, for similar reasons to those in the case of the alkanediyl group, an oxymethanediyl group and an oxy-1,1-ethanediyl group are preferred, and an oxymethanediyl group is particularly preferred.

Examples of the bivalent aromatic hydrocarbon group represented by the $A^3$ include a benzenediyl group, a methylbenzenediyl group, a dimethylbenzenediyl group, a trimethylbenzenediyl group, an ethylbenzenediyl group, a diethylbenzenediyl group, a naphthalenediyl group, a methylnaphthalenediyl group, an anthracenediyl group, a phenanthrenediyl group, and the like. Among these, for similar reasons to those in the case of the alkanediyl group, a benzenediyl group and a naphthalenediyl group are preferred, and a benzenediyl group is particularly preferred.

Examples of the alkyl group having 1 to 4 carbon atoms represented by the $R^A$ and $R^B$ include a methyl group, an ethyl group, a n-propyl group, an i-propyl group, a n-butyl group, an i-butyl group, a sec-butyl group, a t-butyl group, and the like. Of these, a methyl group and an ethyl group are preferred, and an ethyl group is particularly preferred.

Examples of the alkyl group having 1 to 6 carbon atoms represented by the $R^C$ include, in addition to the examples of the alkyl group having 1 to 4 carbon atoms represented by the $R^A$ and $R^B$, a n-pentyl group, an i-pentyl group, a sec-pentyl group, a neo-pentyl group, a n-hexyl group, an i-hexyl group, a sec-hexyl group, a neo-hexyl group, and the like. Among these, a methyl group and an ethyl group are preferred, and a methyl group is particularly preferred.

Examples of the monovalent group represented by the above formula (Y1) include an epoxy group, an epoxymethyl group, an epoxyethyl group, an epoxypropyl group, a glycidyl group, a glycidyloxy group, an epoxyethyloxy group, an epoxypropyloxy group, and the like. Among these, an epoxy group, an epoxymethyl group and a glycidyl group are preferred, and a glycidyl group is particularly preferred.

Examples of the monovalent group represented by the above formula (Y2) include a 3-methyl-3-oxetanyl group, a 3-methyl-3-oxetanylmethyl group, a 3-methyl-3-oxetanylmethyloxy group, a 3-ethyl-3-oxetanyl group, a 3-ethyl-3-oxetanylmethyl group, a 3-ethyl-3-oxetanylethyloxy group, a 3-ethyl-3-oxetanylpropyl group, a 3-ethyl-3-oxetanylpropyloxy group, and the like. Among these, a 3-methyl-3-oxetanylmethyloxy group and a 3-ethyl-3-oxetanylmethyloxy group are preferred, and a 3-ethyl-3-oxetanylmethyloxy group is more preferred.

Examples of the monovalent group represented by the above formula (Y3) include a methoxymethylamino group, a methyl(methoxymethyl)amino group, an ethyl(methoxymethyl)amino group, an ethyl(methoxymethyl)amino group, an i-propyl(i-propoxy)amino group, and the like. Among these, a methoxymethylamino group, a methyl(methoxymethyl)amino group and an ethyl(methoxymethyl)amino group are preferred, and an ethyl(methoxymethyl)amino group is more preferred.

Examples of the monovalent group represented by the above formula (Y4) include a 2-hydroxymethylphenyl group, a 3-hydroxymethylphenyl group, a 4-hydroxymethylphenyl group, a 6-hydroxymethyl-2-naphthyl group, a 4-hydroxymethyl-1-naphthyl group, and the like. Of these, a 2-hydroxymethylphenyl group and a 4-hydroxymethylphenyl group are more preferred.

Specific examples of the crosslinkable compound (A1) include the compounds represented by the above formula (1).

In the above formula (1), $Y^1$ and $Y^2$ each independently represent a crosslinkable functional group; X represents an alkali-cleavable functional group; $R^1$ represents a linking group having a valency of (n1+1); $R^2$ represents a linking group having a valency of (n2+m); n1 is an integer of 1 to 3; n2 is an integer of 0 to 3; m is an integer of 1 to 3; wherein, n1, m and n2 satisfy the formula of: (n1×m+n2)≤2, and provided that $Y^1$, $Y^2$, X or $R^1$ is each present in plural number, the $Y^1$, $Y^2$, X or $R^1$ present in plural number may be each the same or different.

Examples of the crosslinkable functional group represented by the $Y^1$ and $Y^2$ include specific examples of the crosslinkable functional group described above.

Examples of the alkali-cleavable functional group represented by the X described above include specific examples of the alkali-cleavable functional group described above.

Examples of the linking group having a valency of (n1+1) (wherein, n1 is an integer of 1 to 3) represented by the $R^1$ described above include groups derived by eliminating 2 to 4 hydrogen atoms from a chain hydrocarbon having 1 to 30 carbon atoms, an alicyclic hydrocarbon having 3 to 30 carbon atoms or an aromatic hydrocarbon having 6 to 30 carbon atoms, or groups derived by combining these with an ether group, a carbonyl group, an imino group or an amide group. Also, the linking group having a valency of (n1+1) may have a substituent.

Specific examples of the chain hydrocarbon having 1 to 30 carbon atoms include:

chain saturated hydrocarbons such as methane, ethane, propane, butane, pentane, hexane, octane, decane, undecane, dodecane, tetradecane, hexadecane and icosane;

alkenes such as ethylene, propylene, butene, pentene, hexene, octene, decene, undecene, dodecene, tetradecene, hexadecane and eicosene;

alkynes such as acetylene, propyne, butyne and octyne;

chain unsaturated hydrocarbons such as e.g., polyene-containing hydrocarbons and the like such as butadiene, hexadiene and octatriene.

Specific examples of the alicyclic hydrocarbon having 3 to 30 carbon atoms include:

monocyclic saturated hydrocarbons such as cyclopropane, cyclobutane, cyclopentane, cyclohexane, cycloheptane, cyclooctane, cyclodecane, methylcyclohexane and ethylcyclohexane;

monocyclic unsaturated hydrocarbons such as cyclobutene, cyclopentene, cyclohexene, cycloheptene, cyclooctene, cyclodecene, cyclopentadiene, cyclohexadiene, cyclooctadiene and cyclodecadiene;

polycyclic saturated hydrocarbons such as bicyclo[2.2.1]heptane, bicyclo[2.2.2]octane, tricyclo[5.2.1.0$^{2,6}$]decane, tricyclo[3.3.1.1$^{3,7}$]decane, tetracyclo[6.2.1.1$^{3,6}$.0$^{2,7}$]dodecane and adamantane;

polycyclic unsaturated hydrocarbons such as bicyclo[2.2.1]heptene, bicyclo[2.2.2]octene, tricyclo[5.2.1.0$^{2,6}$]decene, tricyclo[3.3.1.1$^{3,7}$]decene and tetracyclo[6.2.1.1$^{3,6}$.0$^{2,7}$]dodecene, and the like.

Specific examples of the aromatic hydrocarbon having 6 to 30 carbon atoms include benzene, biphenyl, terphenyl, toluene, ethylbenzene, cyclohexylbenzene, naphthalene, 2,2'-diphenyl propane, and the like.

Examples of the substituent which may be included in the group having a valency of (n1+1) include an alkyl group, a cycloalkyl group, an aryl group, a halogen atom such as a fluorine atom, a chlorine atom, a bromine atom or an iodine atom, a hydroxyl group, a cyano group, an amino group, and the like.

Examples of preferable linking group having a valency of (n1+1) represented by the $R^1$ described above include chain hydrocarbon groups having 1 to 4 carbon atoms, alicyclic hydrocarbon groups having 4 to 12 carbon atoms and aromatic hydrocarbons group having 6 to 18 carbon atoms, and these hydrocarbon group in which a part or all of hydrogen atoms are substituted with a substituent. Of these, groups having a valency of (n1+1) derived by eliminating (n1+1) hydrogen atoms from benzene, naphthalene, or 2,2'-diphenyl propane, and groups derived by substituting a part or all of hydrogen atoms of these groups with an alkyl group, a cycloalkyl group, an aryl group, a halogen atom, a hydroxyl group, a cyano group or an amino group are more preferred.

Examples of, and examples of preferable linking group having a valency of (n2+m) (wherein n2 is 0 to 3, and m is 1 to 3) represented by the $R^2$ described above include those exemplified in connection with the $R^1$ described above in which n1 is (n2+m).

Since the crosslinkable compound (A1) has two or more crosslinkable functional groups, the above denotations of n1, n2 and m satisfy the formula of: (n1×m+n2)≥2. Of these, in light of ease in crosslinking of the crosslinkable compound (A1), and ease in construction of the crosslinkable compound (A1), (n1×m+n2) is preferably 2.

Examples of suitable crosslinkable compound (A1) represented by the above formula (1) include compounds represented by the above formula (1-1), provided that m is 2, n1 is 1 and n2 is 0, and compounds represented by the above formula (1-2), provided that m is 1, n1 is 1 and n2 is 1.

In the above formulae (1-1) and (1-2), $Y^{11}$, $Y^{12}$, $Y^{1'}$ and $Y^{2'}$ each independently represent a monovalent group each represented by the above formulae (Y1) to (Y4); $X^1$, $X^2$ and $X'$ represent an ester group; $R^{11}$, $R^{12}$, $R^{1'}$, $R^{20}$ and $R^{20'}$ each independently represent a phenylene group, a naphthylene group, an isopropylidenediphenylene group or an alkanediyl group having 1 to 6 carbon atoms which is unsubstituted or substituted with a fluorine atom, wherein a part or all of hydrogen atoms of the aromatic ring of the phenylene group, the naphthylene group and the isopropylidenediphenylene group are unsubstituted or substituted by an alkyl group, a cycloalkyl group, an aryl group, a halogen atom, a hydroxyl group, a cyano group or an amino group.

Details of the monovalent group each represented by the above formulae (Y1) to (Y4) represented by the $Y^{11}$, $Y^{12}$, $Y^{1'}$ and $Y^{2'}$ described above are as defined in connection with the aforementioned crosslinkable functional group.

The phenylene group, the naphthylene group and the isopropylidenediphenylene group represented by the $R^{11}$, $R^{12}$, $R^{1'}$, $R^{20}$ and $R^{20'}$ described above are groups derived by eliminating two hydrogen atom from benzene, naphthalene and 2,2'-diphenyl propane, in the case in which: n1 is 1 in the linking group having a valency of (n1+1) represented by the $R^1$ described above; and n2 is 0 and m is 2 in the linking group having a valency of (n2+m) represented by the $R^2$ described above.

Examples of the alkanediyl group having 1 to 6 carbon atoms represented by the $R^{11}$, $R^{12}$, $R^{1'}$, $R^{20}$ and $R^{20'}$ described above include a methanediyl group, an ethanediyl group, a linear and branched propanediyl group, a butanediyl group, a pentanediyl group, a hexanediyl group, and the like. Among these, a methanediyl group and an ethanediyl group are preferred in light of attaining the resultant resist underlayer film having more rigid molecules and having a higher carbon content, and being superior in the strength and having enhanced etching resistance.

In addition, examples of the alkanediyl group having 1 to 6 carbon atoms substituted with a fluorine atom, represented by the $R^{11}$, $R^{12}$, $R^{1'}$, $R^{20}$ and $R^{20'}$ described above include a fluoromethanediyl group, a difluoromethanediyl group, a fluoroethanediyl group, a difluoroethanediyl group, a perfluoroethanediyl group, a linear or branched difluoropropanediyl group, a tetrafluoropropanediyl group, a perfluoropropanediyl group, a difluorobutanediyl group, a tetrafluorobutanediyl group, a perfluorobutanediyl group, a difluoropentanediyl group, a tetrafluoropentanediyl group, a perfluoropentanediyl group, a difluoropentanediyl group, a tetrafluoropentanediyl group, a perfluoropentanediyl group, and the like. Among these, since alkali-cleavability of an adjacent ester group is improved groups in which all hydrogen atoms of the terminal carbon atom adjacent to the ester group are substituted with a fluorine atom are preferred, and a perfluoroalkanediyl group is more preferred. Specifically, a difluoromethanediyl group, a perfluoroethanediyl group, a 1,1,3,3-tetrafluoropropanediyl group, a perfluoropropanediyl group, a 1,1,4,4-tetrafluorobutanediyl group, a perfluorobutanediyl group, a 1,1,5,5-tetrafluoropentanediyl group, a perfluoropentanediyl group, a 1,1,6,6-tetrafluorohexanediyl group and a perfluorohexanediyl group are preferred, and a difluoromethanediyl group, a perfluoroethanediyl group, perfluoropropanediyl group, a perfluorobutanediyl group, perfluoropentanediyl group and a perfluorohexanediyl group are more preferred.

Specific examples of the crosslinkable compound (A1) represented by the above formula (1-1) include compounds represented by the following formulae:

[chemical formula 5]

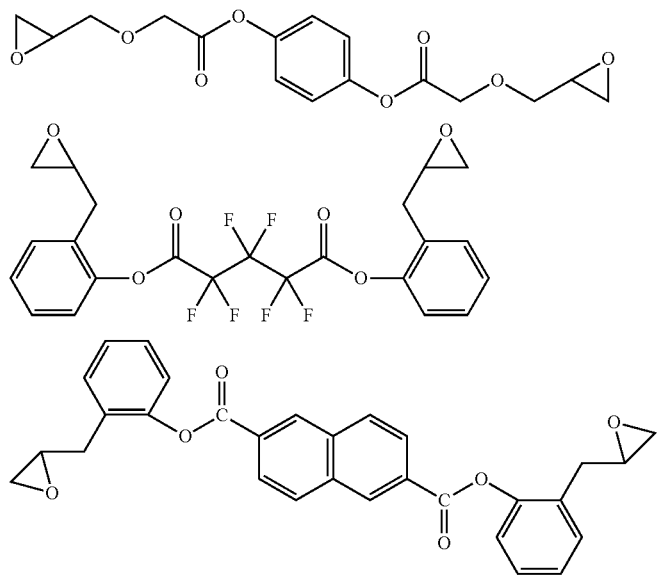

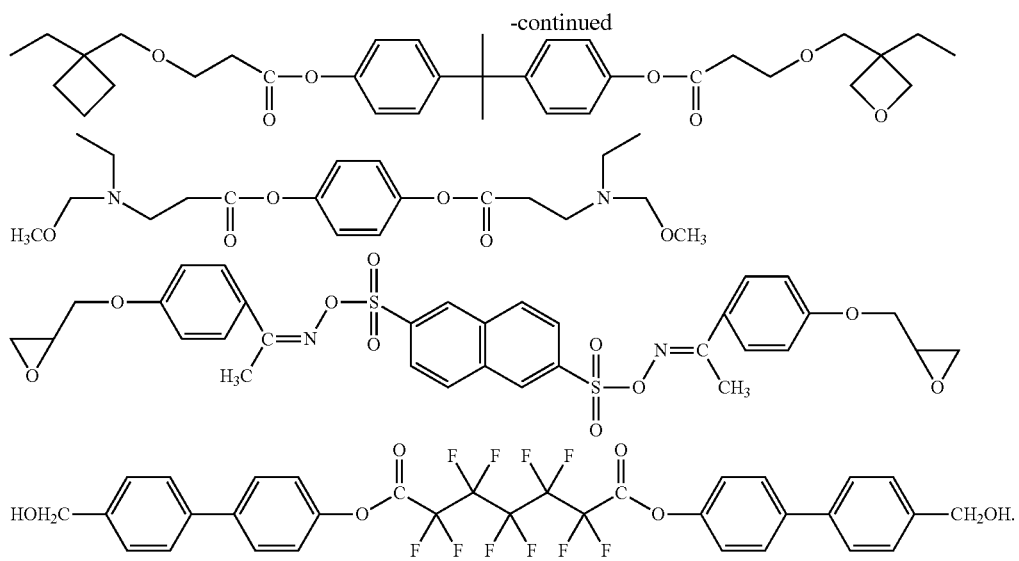
Also, specific examples of the crosslinkable compound (A1) represented by the above formula (1-2) include compounds each represented by the following formulae:
[chemical formula 6]
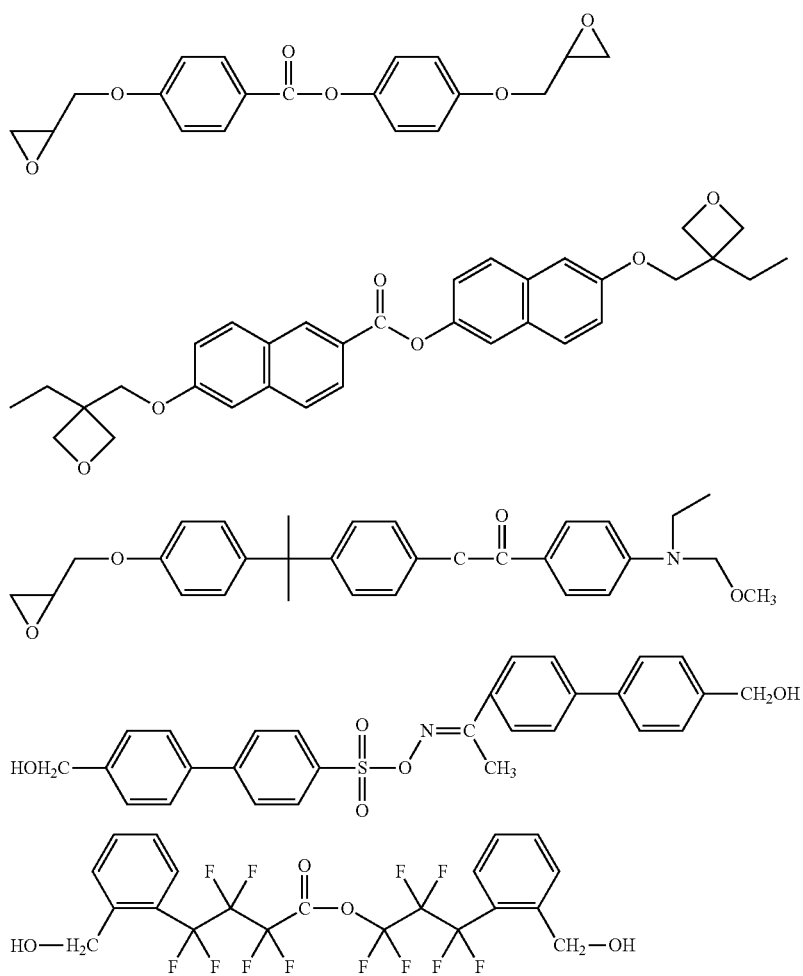

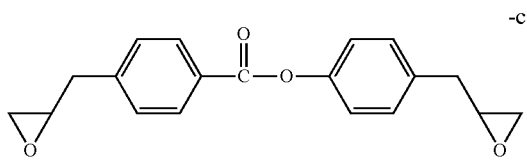
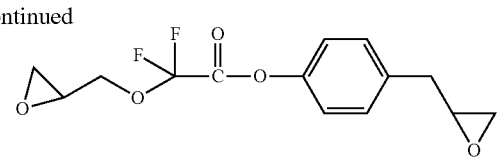

The composition for forming a resist underlayer film may contain either one type, or two or more types of the crosslinkable compound (A1).

The content of the crosslinkable compound (A1) in the composition for forming a resist underlayer film is, in light of enhancement of the strength of the underlayer film, preferably 1% by mass to 50% by mass, and more preferably 5% by mass to 30% by mass in terms of the solid content in the composition, i.e., the content of the crosslinkable compound (A1) with respect to the total amount of the components other than the organic solvent (C) described later.

Also, the content of the crosslinkable compound (A1) with respect to 100 parts by mass of the polymer (B) described later is preferably no less than 5 parts by mass, and more preferably no less than 7 parts by mass.

<(A2) Polymer>

The polymer (A2) has an alkali-cleavable functional group. When the compound (A) is a polymer, the strength of the resist underlayer film formed in the method for forming a pattern can be enhanced.

The polymer (A2) is not particularly limited as long as it has an alkali-cleavable functional group. Also, the position of the alkali-cleavable functional group in the polymer is not particularly limited. For example, the alkali-cleavable functional group may be incorporated in the main chain of the polymer, or the alkali-cleavable functional group may be included in the side chain or the like bound to the main chain of the polymer. When the alkali-cleavable functional group is incorporated in the main chain of the polymer, cleavage of the alkali-cleavable functional group leads to decomposition of the main chain of the polymer into smaller units. Thus, each unit will have a polar group, thereby enabling ease in removal of the resultant resist underlayer film with an alkali liquid to be improved.

Examples of the polymer (A2) that includes the alkali-cleavable functional group in the main chain of the polymer include those represented by the following formula (a2-1):

[chemical formula 7]

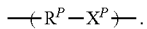

(a2-1)

In the above formula (a2-1), $R^P$ represents a bivalent linking group; and $X^P$ represents an alkali-cleavable functional group.

Examples of the bivalent linking group represented by the $R^P$ described above include examples of the linking group $R^1$ in which n1 is 2 in the above formula (1).

The alkali-cleavable functional group represented by $X^P$ may include the examples of X in the above formula (1).

In addition, self-crosslinked products of the crosslinkable compound (A1) represented by the above formula (1), and cross-linked polymers formed by crosslinking of (B) a polymer and/or (E) a crosslinkable compound described later with the crosslinkable compound (A1) represented by the above formula (1) are also included in examples of suitable polymer (A2) having an alkali-cleavable functional group in the main chain.

The polymer (A2) preferably has a structure unit (P) that includes an aromatic group or an alicyclic group. When the polymer (A2) has the structure unit (P) that includes an aromatic group or an alicyclic group, the carbon content of the resultant resist underlayer film can be increased, and the etching resistance can be enhanced.

[Structure Unit (P)]

The structure unit (P) includes an aromatic group or alicyclic group. The structure unit (P) is not particularly limited as long as it includes an aromatic group or an alicyclic group, but a structure unit derived from at least one hydrocarbon selected from the group consisting of acenaphthylene, naphthalene, fluorene, indene and nortricyclene is preferred. When the polymer (A2) has a structure unit derived from the aforementioned specific hydrocarbon as the structure unit (P), the carbon content of the resultant resist underlayer film can be further increased, and as a result, the etching resistance of the resist underlayer film can be further enhanced.

The polymer (A2) having the structure unit (P) is not particularly limited as long as it has the structure unit (P) and the alkali-cleavable functional group, and for example, an acenaphthylene resin, a naphthalene novolak resin, a fluorine novolak resin, an indene resin, a nortricyclene resin, and the like may be included.

[Acenaphthylene Resin]

The acenaphthylene resin is exemplified by polymers having a structure unit represented by the following formula (a2-2-1):

[chemical formula 8]

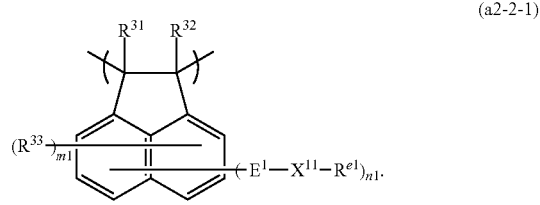

(a2-2-1)

In the above formula (a2-2-1), $E^1$ represents a single bond or a bivalent linking group; $X^{11}$ represents an alkali-cleavable functional group; $R^{e1}$ represents a monovalent organic group; n1 is an integer of 1 to 6, and provided that n1 is 2 or greater, $E^1$, $X^{11}$ and $R^{e1}$ present in plural number may be each the same or different; $R^{31}$ and $R^{32}$ each independently represent a hydrogen atom, a halogen atom or a monovalent organic group; $R^{33}$ represents a hydrogen atom, a halogen atom or a monovalent organic group; m1 is an integer of 0 to 5, and provided that m1 is 2 or greater, $R^{33}$ present in plural number may be the same or different; and n1 and m1 satisfy the formula of:

$$1 \leq n1 + m1 \leq 6.$$

Examples of the bivalent linking group represented by the $E^1$ described above include examples of the linking group $R^1$ in which n1 is 1 in the above formula (1).

The alkali-cleavable functional group represented by the $X^{11}$ described above may include the examples of X in the above formula (1).

Examples of the monovalent organic group represented by the $R^{e1}$ described above include an alkyl group having 1 to 30 carbon atoms, a cycloalkyl group having 3 to 30 carbon atoms, an aryl group having 6 to 30 carbon atoms, an aralkyl group having 7 to 30 carbon atoms, and the like. A part or all of hydrogen atoms of these alkyl group, cycloalkyl group, aryl group and aralkyl group are unsubstituted or substituted by a fluorine atom, an aryl group or the like.

The halogen atom represented by the $R^{31}$ to $R^{33}$ described above may include, for example, a fluorine atom, a chlorine atom, a bromine atom, an iodine atom, and the like.

Examples of the monovalent organic group represented by the $R^{31}$ to $R^{33}$ described above include an alkyl group having 1 to 6 carbon atoms, an alkoxy group having 1 to 6 carbon atoms, alkoxycarbonyl group having 2 to 10 carbon atoms, or an aryl group having 6 to 14 carbon atoms, and the like. A part or all of hydrogen atoms of these alkyl group, alkoxy group, alkoxycarbonyl group and aryl group are unsubstituted or substituted by a substituent.

Examples of the alkyl group having 1 to 6 carbon atoms include a methyl group, an ethyl group, a n-propyl group, an i-propyl group, a n-butyl group, a 2-methylpropyl group, a 1-methylpropyl group, a t-butyl group, and the like.

Examples of the alkoxy group having 1 to 6 carbon atoms include a methoxy group, an ethoxy group, a n-propoxy group, an i-propoxy group, a n-butoxy group, a 2-methylpropoxy group, a 1-methylpropoxy group, a t-butoxy group, and the like.

Examples of the alkoxycarbonyl group having 2 to 10 carbon atoms include a methoxycarbonyl group, an ethoxycarbonyl group, a n-propoxycarbonyl group, an i-propoxycarbonyl group, a n-butoxycarbonyl group, a 2-methylpropoxycarbonyl group, a 1-methylpropoxycarbonyl group, a t-butoxycarbonyl group, and the like.

Examples of the aryl group having 6 to 14 carbon atoms include a phenyl group, a naphthyl group, and the like.

Examples of the substituent which may be included in the $R^{31}$ to $R^{33}$ described above include a halogen atom such as a fluorine atom, a chlorine atom, a bromine atom or an iodine atom, a hydroxyl group, an alkyl group having 1 to 9 carbon atoms, an aryl group having 6 to 22 carbon atoms, and the like.

In addition, examples of the acenaphthylene resin as the polymer (A2) also include polymers having a structure unit represented by the following formula (b-1), and a structure unit that includes the alkali-cleavable functional group.

[chemical formula 9]

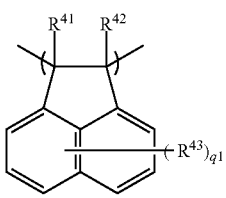

(b-1)

In the above formula (b-1), $R^{41}$ and $R^{42}$ are as defined in connection with $R^{31}$ and $R^{32}$ in the above formula (a2-2-1); $R^{43}$ is as defined in connection with $R^{33}$ in the above formula (a2-2-1); q1 is an integer of 0 to 6, and provided that q1 is 2 or greater, $R^{43}$ present in plural number may be the same or different.

The structure unit that includes the alkali-cleavable functional group is exemplified by a structure unit represented by the following formula (a2-2-X):

[chemical formula 10]

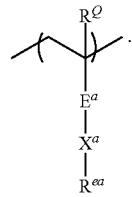

(a2-2-X)

In the above formula (a2-2-X), $R^Q$ represents a hydrogen atom, a halogen atom or a monovalent organic group; $E^a$ represents a single bond or a bivalent linking group; $X^a$ represents an alkali-cleavable functional group; and $R^{ea}$ represents a monovalent organic group.

Each example of the halogen atom and the monovalent organic group represented by the $R^Q$ described above include the examples of $R^{31}$ and $R^{32}$ in the above formula (a2-2-1).

Each example of the bivalent linking group represented by the $E^a$, the alkali-cleavable functional group represented by $X^a$, and the monovalent organic group represented by $R^{ea}$ include the examples of $E^1$, $X^{11}$ and $R^{e1}$ in the above formula (a2-2-1). The bivalent linking group represented by the $E^a$ described above is preferably a bivalent aromatic hydrocarbon group.

The acenaphthylene resin can be obtained by polymerization through subjecting a compound having an acenaphthylene skeleton to an appropriate polymerization system such as block polymerization or solution polymerization by radical polymerization, anion polymerization, cation polymerization or the like. Alternatively, as is disclosed in paragraph nos. [0008] to [0031] of Japanese Unexamined Patent Application, Publication No. 2002-296789, the acenaphthylene resin can be also obtained by allowing the polymer of the compound having an acenaphthylene skeleton to react with paraformaldehyde under an acidic condition, and the like.

[Naphthalene Novolak Resin]

The naphthalene novolak resin is exemplified by polymers having a structure unit represented by the following formula (a2-2-2):

[chemical formula 11]

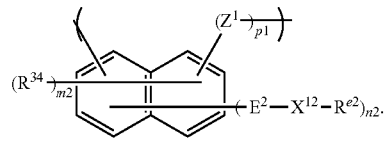

(a2-2-2)

In the above formula (a2-2-2), $E^2$ represents a single bond or a bivalent linking group; $X^{12}$ represents an alkali-cleavable functional group; $R^{e2}$ represents a monovalent organic group; n2 is an integer of 1 to 6, and provided that n2 is 2 or greater, $E^2$, $X^{12}$ and $R^{e2}$ present in plural number may be each the same or different; $R^{34}$ represents a hydrogen atom, a halogen atom, a hydroxyl group or a monovalent organic group; m2 is an integer of 0 to 5, and provided that m2 is 2 or greater, $R^{34}$ present in plural number may be the same or different; $Z^1$ represents a methylene group, an alkylene group having 2 to 20 carbon atoms, an arylene group having 6 to 14 carbon atoms, or an oxyalkanediyl group; a part or all of hydrogen atoms of the methylene group, the alkylene group, the arylene group and the oxyalkanediyl group are unsubstituted or substituted by a substituent; p1 is an integer of 1 to 6, and provided that p1 is 2 or greater, $Z^1$ present in plural number may be the same or different; and n2, m2 and p1 satisfy the formula of: $1 \leq (n1+m1+p1) \leq 7$.

Each example of the bivalent linking group represented by the $E^2$, the alkali-cleavable functional group represented by $X^{12}$, and the monovalent organic group represented by $R^{e2}$ each include the examples of $E^1$, $X^{11}$ and $R^{e1}$ in the above formula (a2-2-1), respectively.

The halogen atom represented by the $R^{34}$ described above may include a fluorine atom, a chlorine atom, a bromine atom, an iodine atom, or the like.

The monovalent organic group represented by the $R^{34}$ described above include an alkyl group having 1 to 6 carbon atoms, an alkoxy group having 1 to 6 carbon atoms, an alkoxycarbonyl group having 2 to 10 carbon atoms, an aryl group having 6 to 14 carbon atoms, a glycidyl ether group, or an alkylglycidyl ether group (wherein, the alkyl moiety has 1 to 6 carbon atoms). A part or all of hydrogen atoms of the alkyl group, the alkoxy group, the alkoxycarbonyl group, the aryl group, the glycidyl ether group and the alkylglycidyl ether group are unsubstituted or substituted by a substituent.

Examples of the alkyl group having 1 to 6 carbon atoms, the alkoxyl group having 1 to 6 carbon atoms, the alkoxycarbonyl group having 2 to 10 carbon atoms and the aryl group having 6 to 14 carbon atoms represented by the $R^{34}$ include the examples in connection with $R^{31}$ to $R^{33}$ in the above formula (a2-2-1).

Examples of the alkylglycidyl ether group represented by $R^{34}$ include a methylglycidyl ether group, an ethylglycidyl ether group, a propylglycidyl ether group, a butylglycidyl ether group, and the like.

Examples of the alkylene group having 2 to 20 carbon atoms represented by $Z^1$ include an ethylene group; propylene groups such as a 1,3-propylene group and a 1,2-propylene group; a tetramethylene group, a pentamethylene group, a hexamethylene group, a 1-methyl-1,3-propylene group, a 2-methyl-1,3-propylene group, a 2-methyl-1,2-propylene group, a 1-methyl-1,4-butylene group, a 2-methyl-1,4-butylene group, and the like.

Examples of the arylene group having 6 to 14 carbon atoms represented by $Z^1$ include a phenylene group, a naphthylene group, an anthrylene group, a phenanthrylene group, and the like.

The alkanediyl chain of the oxyalkanediyl group represented by $Z^1$ preferably has 2 to 20 carbon atoms. Specific examples of the oxyalkanediyl group include an oxyethanediyl group; oxypropanediyl groups such as an oxy-1,3-propanediyl group and an oxy-1,2-propanediyl group; an oxytetramethylene group, an oxypentamethylene group, an oxyhexamethylene group, and the like.

The $R^{34}$ and $Z^1$ described above may have a substituent. Examples of the substituent include a halogen atom, a hydroxyl group, an alkyl group having 1 to 9 carbon atoms, an aryl group having 6 to 22 carbon atoms, and the like. Examples of the halogen atom include fluorine, chlorine, bromine, iodine, and the like. Examples of the alkyl group having 1 to 9 carbon atoms include a methyl group, an ethyl group, a n-propyl group, an i-propyl group, a n-butyl group, a 2-methylpropyl group, a 1-methylpropyl group, a t-butyl group, and the like. Examples of the aryl group having 6 to 22 carbon atoms include a phenyl group, a naphthyl group, and the like.

In addition, examples of the naphthalene novolak resin as the polymer (A2) include polymers having a structure unit represented by the following formula (b-2), and a structure unit that includes an alkali-cleavable functional group. Examples of the structure unit that includes the alkali-cleavable functional group include structure units represented by the above formula (a2-2-X).

[chemical formula 12]

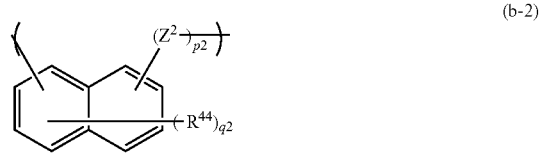

(b-2)

In the above formula (b-2), $R^{44}$ is as defined in connection with $R^{33}$ in the above formula (a2-2-2); q2 is an integer of 0 to 6; $Z^2$ is as defined in connection with $Z^1$ in the above formula (a2-2-2); p2 is an integer of 1 to 7, and provided that p2 is 2 or greater, $Z^2$ present in plural number may be the same or different.

The naphthalene novolak resin can be obtained by reacting a naphthol such as α-naphthol, β-naphthol, 1,5-dihydroxynaphthalene or 2,7-dihydroxynaphthalene with an aldehyde or a divinyl compound using an acidic catalyst or the like.

As the aldehyde, one, or at least two types of aldehyde may be included among the aldehyde sources such as formaldehyde, paraformaldehyde, trioxane and the like. Examples of the divinyl compound include divinylbenzene, dicyclopentadiene, tetrahydroindene, 4-vinylcyclohexene, 5-vinylnorborna-2-ene, α-pinene, β-pinene, limonene, 5-vinylnorbornadiene, and the like.

[Fluorene Novolak Resin]

The fluorene novolak resin is exemplified by polymers having a structure unit represented by the following formula (a2-2-3):

[chemical formula 13]

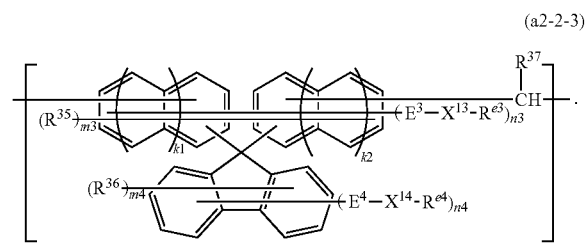

(a2-2-3)

In the above formula (a2-2-3), $E^3$ and $E^4$ each independently represent a single bond or bivalent linking group; $X^{13}$ and $X^{14}$ each independently represent an alkali-cleavable functional group; $R^{e3}$ and $R^{e4}$ each independently represent a monovalent organic group; n3 is an integer of 0 to 8; n4 is an integer of 0 to 8; wherein, the cases in which n3 and n4 are both 0 are excluded, and provided that n3 or n4 is no less than 2, $E^3$, $E^4$, $X^{13}$, $X^{14}$, $R^{e3}$ and $R^{e4}$ present in plural number may be each the same or different; $R^{35}$ and $R^{36}$ each independently represent a hydrogen atom, a halogen atom, a hydroxyl group or a monovalent organic group; m3 is an integer of 0 to 8; m4 is an integer of 0 to 8, and provided that m3 or m4 is no less than 2, $R^{35}$ and $R^{36}$ present in plural number may be each the same or different; $R^{37}$ represents a hydrogen atom or a monovalent organic group; n3 and m3 satisfy the formula of: $0 \leq n3+m3 \leq 12$; n4 and m4 satisfy the formula of: $0 \leq n3+m3 \leq 12$; and k1 and k2 are each independently 0 or 1.

Each example of the bivalent linking group represented by the $E^3$ and $E^4$, the alkali-cleavable functional group represented by the $X^{13}$ and $X^{14}$, and the monovalent organic group represented by the $R^{e3}$ and $R^{e4}$ include the examples of $E^1$, $X^{11}$ and $R^{e1}$ in the above formula (a2-2-1), respectively.

Each example of the halogen atom, and the monovalent organic group represented by $R^{35}$ and $R^{36}$ includes the examples of $R^{34}$ in the above formula (a2-2-2), respectively.

Examples of the monovalent organic group represented by $R^{37}$ include linear or branched alkyl groups having 1 to 10 carbon atoms, cycloalkyl groups having 3 to 10 carbon atoms, aryl groups having 6 to 10 carbon atoms, and the like.

In the above formula (a2-2-3), k1 is preferably 0, and k2 is preferably 0.

In addition, examples of the fluorene novolak resin as the polymer (A2) include polymers having a structure unit represented by the following formula (b-3), and a structure unit that includes an alkali-cleavable functional group. Examples of the structure unit that includes the alkali-cleavable functional group include structure units represented by the above formula (a2-2-X).

[chemical formula 14]

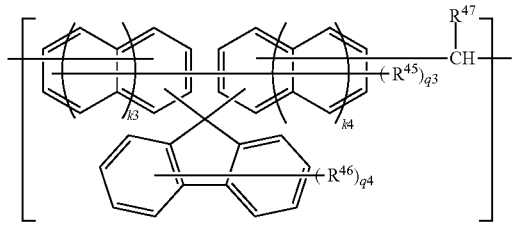

(b-3)

In the above formula (b-3), $R^{45}$ and $R^{46}$ are as defined in connection with $R^{35}$ and $R^{36}$ in the above formula (a2-2-3); q3 is an integer of 0 to 8; q4 is an integer of 0 to 8, and provided that q3 or q4 is no less than 2, $R^{45}$ and $R^{46}$ present in plural number may be each the same or different; $R^{47}$ is as defined in connection with $R^{37}$ in the above formula (a2-2-3); and k3 and k4 are each independently 0 or 1.

In the above formula (b-3), k3 is preferably 0, and k4 is preferably 0.

The fluorene novolak resin can be obtained by reacting, for example, a phenol compound having a fluorine structure such as 4,4'-(9H-fluorene-9-ylidene)bisphenol with an aldehyde or a divinyl compound using an acidic catalyst. The aldehyde and the divinyl compound etc., employed may be similar to those in the case of the naphthalene novolak resin described above.

[Indene Resin]

The indene resin is exemplified by polymers having a structure unit represented by the following formula (a2-2-4):

[chemical formula 15]

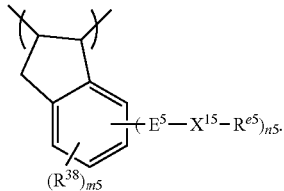

(a2-2-4)

In the above formula (a2-2-4), $E^5$ represents a single bond or a bivalent linking group; $X^{15}$ represents an alkali-cleavable functional group; $R^{e5}$ represents a monovalent organic group; n5 is an integer of 1 to 4, and provided that n5 is no less than 2, $E^5$, $X^{15}$ and $R^{e5}$ present in plural number may be each the same or different; $R^{38}$ represents a hydrogen atom, a halogen atom, a hydroxyl group or a monovalent organic group; m5 is an integer of 0 to 4, and provided that m5 is no less than 2, $R^{38}$ present in plural number may be the same or different; and n5 and m5 satisfy the formula of: $1 \leq n1+m1 \leq 4$.

Each example of the bivalent linking group represented by the $E^5$, the alkali-cleavable functional group represented by $X^{15}$, and the monovalent organic group represented by $R^{e5}$ include the examples of $E^1$, $X^{11}$ and $R^{e1}$ in the above formula (a2-2-1), respectively.

Each example of the halogen atom, and the monovalent organic group represented by $R^{38}$ includes the examples of $R^{31}$ to $R^{33}$ in the above formula (a2-2-1), respectively.

In addition, examples of the indene resin as the polymer (A2) include polymers having a structure unit represented by the following formula (b-4), and a structure unit that includes an alkali-cleavable functional group. Examples of the structure unit that includes the alkali-cleavable functional group include structure units represented by the above formula (a2-2-X).

[chemical formula 16]

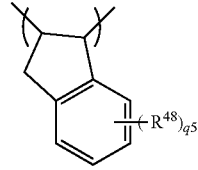

(b-4)

In the above formula (b-4), $R^{48}$ is as defined in connection with $R^{38}$ in the above formula (a2-2-4); q5 is an integer of 0 to 4, and provided that q5 is no less than 2, $R^{48}$ present in plural number may be the same or different.

The indene resin can be obtained by polymerization through subjecting a substituted or unsubstituted indene to an appropriate polymerization system such as block polymerization or solution polymerization by radical polymerization, cation polymerization or the like.

[Nortricyclene Resin]

The nortricyclene resin is exemplified by polymers having a structure unit represented by the following formula (a2-2-5):

[chemical formula 17]

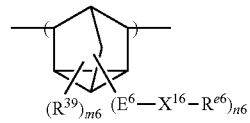

(a2-2-5)

In the above formula (a2-2-5), $E^6$ represents a single bond or a bivalent linking group; $X^{16}$ represents an alkali-cleavable functional group; $R^{e6}$ represents a monovalent organic group; n6 is an integer of 1 to 8, and provided that n6 is no less than 2, $E^6$, $X^{16}$ and $R^{e6}$ present in plural number may be each the same or different; $R^{39}$ represents a hydrogen atom, a halogen atom, a hydroxyl group or a monovalent organic group; m6 is an integer of 0 to 8, and provided that m6 is no less than 2, $R^{39}$ represent in plural number may be the same or different; and n6 and m6 satisfy the formula of: $1 \leq n1+m1 \leq 8$.

Each example of the bivalent linking group represented by the $E^6$, the alkali-cleavable functional group represented by $X^{16}$, and the monovalent organic group represented by $R^{e6}$ include the examples of $E^1$, $X^{11}$ and $R^{e1}$ in the above formula (a2-2-1), respectively.

Each example of the halogen atom, and the monovalent organic group represented by $R^{39}$ includes the examples of $R^{31}$ to $R^{33}$ in the above formula (a2-2-1), respectively.

In addition, examples of the nortricyclene resin as the polymer (A2) include polymers having a structure unit represented by the following formula (b-5), and a structure unit that includes an alkali-cleavable functional group. Examples of the structure unit that includes the alkali-cleavable functional group include structure units represented by the above formula (a2-2-X).

[chemical formula 18]

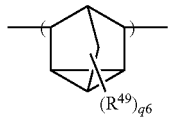

(b-5)

In the above formula (b-5), $R^{49}$ is as defined in connection with $R^{39}$ in the above formula (a2-2-5); q6 is an integer of 0 to 8, and provided that q6 is no less than 2, $R^{49}$ present in plural number may be the same or different.

The nortricyclene resin can be obtained by polymerization through subjecting a substituted or unsubstituted norbornadiene to an appropriate polymerization system such as block polymerization or solution polymerization by radical polymerization, cation polymerization or the like.

The polymer (A2) has a polystyrene equivalent weight average molecular weight (hereinafter, may be also referred to as "Mw") of preferably 500 to 100,000, more preferably 1,000 to 50,000, and still more preferably 1,200 to 40,000.

The polymer (A2) has a polystyrene equivalent number average molecular weight (hereinafter, may be also referred to as "Mn") of preferably 400 to 80,000, more preferably 800 to 40,000, and still more preferably 1,000 to 35,000.

The ratio of Mw to Mn (Mw/Mn ratio) of the polymer (A2) is usually 1 to 5, and more preferably 1 to 3. It is to be noted that the values of Mw and Mn may be determined by measuring on gel permeation chromatography (GPC) using mono-dispersed polystyrene as a standard sample.

The composition for forming a resist underlayer film may contain either one type, or two or more types of the polymer (A2).

The proportion of the polymer (A2) in the composition for forming a resist underlayer film is, in light of enhancement of the strength of the underlayer film, preferably 1% by mass to 50% by mass, and more preferably 5% by mass to 30% by mass in terms of the solid content in the composition, i.e., the content of the polymer (A2) with respect to the total amount of the components other than the organic solvent (C) described later.

<Method for Synthesizing Compound (A)>

Among the foregoing crosslinkable compounds (A1), the compound represented by the above formula (1-1) (i.e., those having a crosslinkable functional group that includes an oxygen atom at the end of the bonding hand side) can be obtained by, for example, as illustrated in the following schema (R1-1), reacting a hydroxyl group-containing compound derived from the crosslinkable functional group with a chlorinated product of a compound containing a carboxyl group or the like derived from the alkali-cleavable functional group in the presence of a base such as 1,8-diazabicyclo[5.4.0]undeca-7-ene to obtain a compound containing a crosslinkable functional group and a carboxyl group or the like, and then reacting the compound obtained and a dihydroxy compound in the presence of a dehydrating agent such as N,N'-dicyclohexyl-carbodiimide, and a base such as N,N'-dimethylaminopyridine.

Also, among the foregoing crosslinkable compounds (A1), the compound represented by the above formula (1-2) (i.e., those having a crosslinkable functional group that includes an oxygen atom at the end of the bonding hand side) can be obtained by, for example, as illustrated in the following schema (R1-2), reacting a compound containing a carboxyl group or the like derived from the alkali-cleavable functional group with an equimolar amount of a dihydroxy compound, in the presence of a base and a dehydrating agent similar to those described above to obtain a dihydroxy compound having an alkali-cleavable functional group; and then reacting the compound thus obtained is reacted with a twice molar amount of a chloro compound derived from a crosslinkable functional group in the presence of a base similar to one described above.

[chemical formula 19]

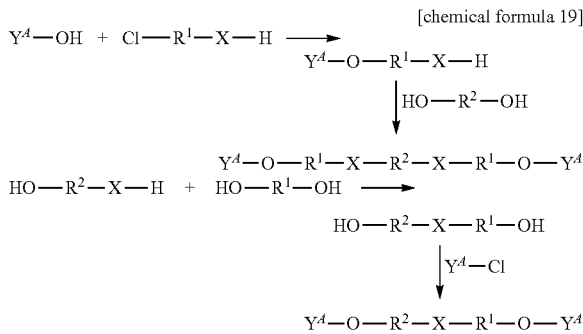

In the above schemata (R1-1) and (R1-2), $R^1$, $R^2$ and X are as defined in the above formula (1); and $Y^4$—O—, is the same as the crosslinkable functional group $Y^1$ and $Y^2$ in the above formula (1).

Among the foregoing polymers (A2), those that include the alkali-cleavable functional group in the main chain of the polymer can be obtained by, for example, permitting dehydrative condensation or the like of a combination of monomers, such as a dicarboxylic acid compound and a dihydroxy compound, etc., capable of forming the alkali-cleavable functional group. Alternatively, among the foregoing polymers (A2), those that include the alkali-cleavable functional group in the side chain, etc., bound to the main chain of the polymer can be obtained by, as described above, polymerizing a monomer that gives a structure unit including the alkali-cleavable functional group, or copolymerizing a monomer that gives a structure unit including the alkali-cleavable functional group with other monomer. Moreover, such a polymer (A2) can be also synthesized by, for example, reacting a polymer having a hydroxyl group and/or a carboxyl group with such a carboxyl group-containing compound or a hydroxyl group-containing compound as a synthetic intermediate ($Y^4$—O—$R^1$—X—H) in the above schema (R1-1) to form an alkali-cleavable functional group.

<(B) Polymer>

The composition for forming a resist underlayer film may contain (B) a polymer not having an alkali-cleavable functional group. When the composition for forming a resist underlayer film contains the polymer (B), the strength of the resultant resist underlayer film can be enhanced. Additionally, by using the crosslinkable compound (A1) and the polymer (B) in combination, a resist underlayer film having enhanced strength can be efficiently formed, and the solubility of the resultant resist underlayer film into the alkali liquid as well as the etching resistance can be both achieved at high levels.

Although the polymer (B) is not particularly limited, it preferably has a structure unit (P) that includes an aromatic group or an alicyclic group, similarly to the polymer (A2). When the polymer (B) has the structure unit (P) that includes an aromatic group or an alicyclic group, the carbon content of the resultant resist underlayer film can be increased, and the etching resistance can be enhanced.

In addition, similarly to the polymer (A2), the structure unit (P) is preferably a structure unit derived from at least one hydrocarbon selected from the group consisting of acenaphthylene, naphthalene, fluorene, indene and nortricyclene. Since the structure unit (P) is derived from the aforementioned specific hydrocarbon, the carbon content of the resultant resist underlayer film can be further increased, and as a result, the etching resistance of the resist underlayer film can be further enhanced.

Examples of the polymer (B) having the structure unit (P) include an acenaphthylene resin having the structure unit represented by the above formula (b-1), a naphthalene novolak resin having the structure unit represented by the above formula (b-2), a fluorene novolak resin having the structure unit represented by the above formula (b-3), an indene resin having the structure unit represented by the above formula (b-4), a nortricyclene resin having the structure unit represented by the above formula (b-5), and the like.

The composition for forming a resist underlayer film may contain either one type, or two or more types of the polymer (B).

The content of the polymer (B) in the composition for forming a resist underlayer film is preferably no less than 10% by mass, and more preferably no less than 20% by mass in terms of the solid content, i.e., with respect to the total amount of the components other than the organic solvent (C) described later.

<(C) Organic Solvent>

The resin composition for forming a resist underlayer film usually contains (C) an organic solvent. The organic solvent is not particularly limited as long as it can dissolve the compound (A), the polymer (B), and other optional component(s) which may be added as needed. The organic solvent (C) is exemplified by an alcohol type solvent, an ether type solvent, a ketone type solvent, an amide type solvent, an ester type solvent and a mixed solvent of these, and the like.

Examples of the alcohol type solvent include:

monoalcohol type solvents such as methanol, ethanol, n-propanol, i-propanol, n-butanol, i-butanol, sec-butanol, tert-butanol, n-pentanol, i-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethyl nonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol and diacetone alcohol;

polyhydric alcohol type solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol and tripropylene glycol;

partially etherified polyhydric alcohol type solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether and dipropylene glycol monopropyl ether, and the like.

Examples of the ether type solvent include diethyl ether, dipropyl ether, dibutyl ether, diphenyl ether, and the like.

Examples of the ketone type solvent include acetone, methyl ethyl ketone, methyl-n-propyl ketone, methyl-n-butyl ketone, diethyl ketone, methyl-1-butyl ketone, methyl-n-pentyl ketone, ethyl-n-butyl ketone, methyl-n-hexyl ketone, di-1-butyl ketone, trimethyl nonanone, cyclopentanone, cyclohexanone, cycloheptanone, cyclooctanone, methyl cyclohexanone, 2,4-pentanedione, acetonyl acetone, acetophenone, and the like.

Examples of the amide type solvent include N,N'-dimethylimidazolidinone, N-methylformamide, N,N-dimethylformamide, N,N-diethylformamide, acetamide, N-methylacetamide, N,N-dimethylacetamide, N-methylpropionamide, N-methylpyrrolidone, and the like.

Examples of the ester type solvent include diethyl carbonate, propylene carbonate, methyl acetate, ethyl acetate, γ-butyrolactone, γ-valerolactone, n-propyl acetate, i-propyl acetate, n-butyl acetate, i-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, acetomethyl acetate, acetoethyl acetate, ethylene acetate glycol monomethyl ether, ethylene acetate glycol monoethyl ether, diethylene acetate glycol monomethyl ether, diethylene acetate glycol monoethyl ether, diethylene acetate glycol mono-n-butyl ether, propylene glycol monomethyl ether acetate, propylene glycol monoethyl ether acetate, propylene glycol monopropyl ether acetate, propylene glycol monobutyl ether acetate, dipropylene glycol monomethyl acetate ether, dipropylene glycol monoethyl acetate ether, diglycol acetate, methoxytriglycol acetate, ethyl propionate, n-butyl propionate, i-amyl propionate, diethyl oxalate, di-n-butyl oxalate, methyl lactate, ethyl lactate, n-butyl lactate, n-amyl lactate, diethyl malonate, dimethyl phthalate, diethyl phthalate, and the like.

Examples of the hydrocarbon type solvent include:

aliphatic hydrocarbon type solvents such as n-pentane, i-pentane, n-hexane, i-hexane, n-heptane, i-heptane, 2,2,4-trimethyl pentane, n-octane, i-octane, cyclohexane and methylcyclohexane;

aromatic hydrocarbon type solvents such as benzene, toluene, xylene, mesitylene, ethylbenzene, trimethylbenzene, methylethylbenzene, n-propylbenzene, i-propylbenzene, diethylbenzene, i-butylbenzene, triethylbenzene, di-1-propylbenzene and n-amylnaphthalene, and the like.

Of these organic solvents (C), the ester type solvent and the ketone type solvent are preferred; ethylene acetate glycol monomethyl ether, ethylene acetate glycol monoethyl ether, propylene glycol monomethyl ether acetate, propylene glycol monoethyl ether acetate, ethyl lactate, n-butyl acetate, ethyl 3-ethoxypropionate, methyl 3-methoxypropionate, γ-butyrolactone, 2-butanone, 2-heptanone and cyclohexanone are more preferred; ethylene acetate glycol monomethyl ether, ethylene acetate glycol monoethyl ether, propylene glycol monomethyl ether acetate and propylene glycol monoethyl ether acetate are even more preferred; and propylene glycol monomethyl ether acetate is particularly preferred. The organic solvent (C) may be used either alone, or two or more types thereof may be used in combination.

The content of the organic solvent (C) in the composition for forming a resist underlayer film falls within the range that gives the concentration of the solid content of the resulting composition being usually 1 to 80% by mass, preferably 3 to 40% by mass, and more preferably 5 to 30% by mass.

<(D) Acid Generator>

(D) an acid generator is a compound that generates an acid by a heat treatment, irradiation with a radioactive ray, or the like. Herein, as the radioactive ray, for example, visible light ray, ultraviolet ray, far ultraviolet ray or the like may be used. When the composition for forming a resist underlayer film contains the acid generator (D), effective formation of crosslinking between molecules at comparatively low temperatures including normal temperatures is enabled. The state of the acid generator (D) contained in the composition for forming a resist underlayer film may be in the form of an acid generating agent (hereinafter, may be also referred to as "acid generating agent (D)") that is a compound as described later, in the form of an acid generation group which was incorporated as a part of the polymer such as the polymer (A2) or other polymer (B), or in the form of a combination of these two.

The temperature of the heat treatment is usually 50 to 450° C., and preferably 200 to 350° C. In addition, the irradiance required for the irradiation with a radioactive ray in the case of ultraviolet rays is usually 1 to 100 mJ, and preferably 10 to 50 mJ.

The acid generating agent (D) is exemplified by onium salts such as iodonium salts, sulfonium salts, tetrahydrothiophenium salts, benzothiazolium salts, ammonium salts and phosphonium salts, as well as acid generating agents of halogen-containing compound type, diazo ketone compound type, sulfone compound type and sulfonic acid compound type, and the like.

Examples of the iodonium salt include diphenyliodonium trifluoromethane sulfonate, diphenyliodonium pyrene sulfonate, diphenyliodonium dodecylbenzene sulfonate, diphenyliodonium nonafluoro n-butane sulfonate, bis(4-tert-butylphenyl)iodonium trifluoromethane sulfonate, bis(4-tert-butylphenyl)iodonium dodecylbenzene sulfonate, bis(4-tert-butylphenyl)iodonium naphthalene sulfonate, bis(4-tert-butylphenyl)iodonium hexafluoroantimonate, bis(4-tert-butylphenyl)iodonium nonafluoro n-butane sulfonate, and the like.

Examples of the sulfonium salt include:

phenylsulfonium salts such as triphenylsulfonium trifluoromethane sulfonate, triphenylsulfonium hexafluoroantimonate, triphenylsulfonium naphthalene sulfonate, triphenylsulfonium nonafluoro n-butane sulfonate, (hydroxyphenyl)benzenemethylsulfonium toluene sulfonate, triphenylsulfonium camphor sulfonate, (4-hydroxyphenyl)benzylmethylsulfonium toluene sulfonate, 4-acetophenyldimethylsulfonium hexafluoroantimonate, 4-acetoxyphenyldimethylsulfonium hexafluoroarsenate, dimethyl-4-(benzyloxycarbonyloxy)phenylsulfonium hexafluoroantimonate, dimethyl-4-(benzoyloxy)phenylsulfonium hexafluoroantimonate, dimethyl-4-(benzoyloxy)phenylsulfonium hexafluoroarsenate and dimethyl-3-chloro-4-acetoxy phenylsulfonium hexafluoroantimonate;

naphthylsulfonium salts such as 1-naphthyldimethylsulfonium trifluoromethane sulfonate, 1-naphthyldiethylsulfonium trifluoromethane sulfonate, 4-cyano-1-naphthyldimethylsulfonium trifluoromethane sulfonate, 4-nitro-1-naphthyldimethylsulfonium trifluoromethane sulfonate, 4-methyl-1-naphthyldimethylsulfonium trifluoromethane sulfonate, 4-cyano-1-naphthyldiethylsulfonium trifluoromethane sulfonate, 4-nitro-1-naphthyldiethylsulfonium trifluoromethane sulfonate, 4-methyl-1-naphthyldiethylsulfonium trifluoromethane sulfonate and 4-hydroxy-1-naphthyldimethylsulfonium trifluoromethane sulfonate;

alkylsulfonium salts such as cyclohexylmethyl(2-oxocyclohexyl)sulfonium trifluoromethane sulfonate, dicyclohexyl(2-oxocyclohexyl)sulfonium trifluoromethane sulfonate and dimethyl(2-oxocyclohexyl)sulfonium trifluoromethane sulfonate;

benzylsulfonium salts such as benzyl-4-hydroxyphenylmethylsulfonium hexafluoroantimonate, benzyl-4-hydroxyphenylmethylsulfonium hexafluorophosphate, 4-acetoxyphenylbenzylmethylsulfonium hexafluoroantimonate, benzyl-4-methoxyphenylmethylsulfonium hexafluoroantimonate, benzyl-2-methyl-4-hydroxyphenylmethylsulfonium hexafluoroantimonate, benzyl-3-chloro-4-hydroxyphenylmethylsulfonium hexafluoroarsenate, 4-methoxybenzyl-4-hydroxyphenylmethylsulfonium hexafluorophosphate, benzoin tosylate and 2-nitrobenzyltosylate;

dibenzylsulfonium salts such as dibenzyl-4-hydroxyphenylsulfonium hexafluoroantimonate, dibenzyl-4-hydroxyphenylsulfonium hexafluorophosphate, 4-acetoxy phenyldibenzylsulfonium hexafluoroantimonate, dibenzyl-4-methoxyphenylsulfonium hexafluoroantimonate, dibenzyl-3-chloro-4-hydroxyphenylsulfonium hexafluoroarsenate, dibenzyl-3-methyl-4-hydroxy-5-tert-butylphenylsulfonium hexafluoroantimonate and benzyl-4-methoxybenzyl-4-hydroxyphenylsulfonium hexafluorophosphate;

substituted benzylsulfonium salts such as p-chlorobenzyl-4-hydroxyphenylmethylsulfonium hexafluoroantimonate, p-nitrobenzyl-4-hydroxyphenylmethylsulfonium hexafluoroantimonate, p-chlorobenzyl-4-hydroxyphenylmethylsulfonium hexafluorophosphate, p-nitrobenzyl-3-methyl-4-hydroxyphenylmethylsulfonium hexafluoroantimonate, 3,5-dichlorobenzyl-4-hydroxyphenylmethylsulfonium hexafluoroantimonate and o-chlorobenzyl-3-chloro-4-hydroxyphenylmethylsulfonium hexafluoroantimonate, and the like.

Examples of the tetrahydrothiophenium salt include 4-hydroxy-1-naphthyltetrahydrothiophenium trifluoromethane sulfonate, 4-methoxy-1-naphthyltetrahydrothiophenium trifluoromethane sulfonate, 4-ethoxy-1-naphthyltetrahydrothiophenium trifluoromethane sulfonate, 4-methoxymethoxy-1-naphthyltetrahydrothiophenium trifluoromethane sulfonate, 4-ethoxymethoxy-1-naphthyltetrahydrothiophenium trifluoromethane sulfonate, 4-(1-methoxyethoxy)-1-naphthyltetrahydrothiophenium trifluoromethane sulfonate, 4-(2-methoxyethoxy)-1-naphthyltetrahydrothiophenium trifluoromethane sulfonate, 4-methoxycarbonyloxy-1-naphthyltetrahydrothiophenium trifluoromethane sulfonate, 4-ethoxycarbonyloxy-1-naphthyltetrahydrothiophenium trifluoromethane sulfonate, 4-n-propoxycarbonyloxy-1-naphthyltetrahydrothiophenium trifluoromethane sulfonate, 4-iso-propoxycarbonyloxy-1-naphthyltetrahydrothiophenium trifluoromethane sulfonate, 4-n-butoxycarbonyloxy-1-naphthyltetrahydrothiophenium trifluoromethane sulfonate, 4-tert-butoxycarbonyloxy-1- naphthyltetrahydrothiophenium trifluoromethane sulfonate, 4-(2-tetrahydrofuranyloxy)-1-naphthyltetrahydrothiophenium trifluoromethane sulfonate, 4-(2-tetrahydropyranyloxy)-1-naphthyltetrahydrothiophenium trifluoromethane sulfonate, 4-benzyloxy-1-naphthyltetrahydrothiophenium trifluoromethane sulfonate and 1-(naphthylacetomethyl)tetrahydrothiophenium trifluoromethane sulfonate, and the like.

Examples of the benzothiazonium salt include 3-benzylbenzothiazolium hexafluoroantimonate, 3-benzylbenzothiazolium hexafluorophosphate, 3-benzylbenzothiazolium tetrafluoroborate, 3-(p-methoxybenzyl)benzothiazolium hexafluoroantimonate, 3-benzyl-2-methylthio benzothiazolium hexafluoroantimonate, 3-benzyl-5-chlorobenzothiazolium hexafluoroantimonate, and the like.

Examples of the halogen-containing compound type acid generating agent include phenyl-bis(trichloromethyl)-s-triazine, methoxyphenyl-bis(trichloromethyl)-s-triazine, naphthyl-bis(trichloromethyl)-s-triazine, and the like.

Examples of the diazo ketone compound type acid generating agent include 1,2-naphthoquinonediazide-4-sulfonyl chloride, 1,2-naphthoquinonediazide-5-sulfonyl chloride, 1,2-naphthoquinonediazide-4-sulfonic acid ester or 1,2-naphthoquinonediazide-5-sulfonic acid ester of 2,3,4,4'-tetrabenzophenone, and the like.

Examples of the sulfone compound type acid generating agent include 4-trisphenacyl sulfone, mesitylphenacyl sulfone, bis(phenylsulfonyl)methane, and the like.

Examples of the sulfonic acid compound type acid generating agent include benzoin tosylate, tristrifluoromethane sulfonate of pyrogallol, nitrobenzyl-9,10-diethoxyanthracene-2-sulfonate, trifluoromethanesulfonyl bicyclo[2,2,1]hept-5-ene-2,3-dicarbodiimide, N-hydroxysuccinimide trifluoromethane sulfonate, 1,8-naphthalenedicarboxylic acid imide trifluoromethane sulfonate, and the like.

Furthermore, in addition to the above-described acid generating agents, ammonium salts such as triethylammonium 1,1,3,3,3-pentafluoro-2-(pivaloyloxy)propane sulfonate, tetrabutylammonium 1,1,3,3,3-pentafluoro-2-(pivaloyloxy)propane sulfonate and tetrabutylammonium trifluoromethane sulfonate, 2,4,4,6-tetrabromocyclohexadienone, and the like may be also exemplified.

Among these acid generating agents (D), iodonium salts and sulfonium salts are preferred, iodonium salts are more preferred, diphenyliodonium salts are still more preferred, and diphenyliodonium trifluoromethane sulfonate is particularly preferred.

In the composition for forming a resist underlayer film, the acid generator (D) may be used either alone, or in combination of two or more thereof.

The content of the acid generating agent (D) in the composition for forming a resist underlayer film is preferably 0.05 to 20 parts by mass, more preferably 0.1 to 10 parts by mass, and still more preferably 0.2 to 5 parts by mass with respect to 100 parts by mass of the total amount of the compound (A) and the polymer (B).

<(E) Crosslinkable Compound>

The composition for forming a resist underlayer film may contain (E) a crosslinkable compound other than the compound (A). When the composition for forming a resist underlayer film contains the crosslinkable compound (E), the resist underlayer film having enhanced strength can be formed.

Examples of the crosslinkable compound (E) include polynuclear phenols, and various commercially available curing agents, and the like. As the crosslinkable compound (E), for example, those described in Japanese Unexamined Patent Application, Publication No. 2004-168748, and the like may be used. These crosslinking agents may be used either alone, or in combination of two or more thereof. Alternatively, a polynuclear phenol and a curing agent may be used in combination.

The content of the crosslinkable compound (E) in the composition for forming a resist underlayer film is, in light of enhancement of the strength of the underlayer film, preferably 1% by mass to 50 parts by mass, and more preferably 5% by mass to 30% by mass with respect to the solid content, i.e., the total amount of the components other than the organic solvent (C), in the composition.

<Other Optional Components>

The composition for forming a resist underlayer film may further contain as other optional components, (F) an accelerator, (G) a binder resin, (H) a radioactive ray absorbing agent, (I) a surfactant, and the like.

<(F) Accelerator>

The accelerator (F) means a one-electron oxidant and the like for sufficiently causing a dehydrogenation reaction required for oxidative crosslinking. The one-electron oxidant means an oxidizing agent that causes transfer of one electron therein. For example, in the case of cerium (IV) nitrate ammonium, a cerium ion (IV) receives one electron to be converted into a cerium ion (III). A radical oxidizing agent such as halogen receives one electron to be converted into an anion. Accordingly, an event of oxidizing a substance to be oxidized (e.g., substrate, catalyst, etc.) by depleting one electron from the substance to be oxidized is referred to as "one electron oxidization", and a component that receives the one electron in this event is referred to as "one-electron oxidant".

Typical examples of the one-electron oxidant include (a) metal compounds, (b) peroxides, (c) diazotized compounds, (d) halogen or halogen acids, and the like.

Examples of the metal compound (a) include metal compounds that include cerium, lead, silver, manganese, osmium, ruthenium, vanadium, thallium, copper, iron, bismuth or nickel. Specific examples include: (a1) cerium salts (for example, quadrivalent cerium salts) such as cerium (IV) ammonium nitrate (CAN: ammonium hexanitratocerate (IV)), cerium (IV) acetate, cerium (IV) nitrate and cerium (IV) sulfate; (a2) lead compounds (e.g., quadrivalent lead compound) such as lead tetraacetate and lead (IV) oxide, (a3) silver compounds such as silver (I) oxide, silver (II) oxide, silver carbonate (Fetizonre agent) and silver nitrate; (a4) manganese compounds such as permanganate, activated manganese dioxide and manganese (III) salts, (a5) osmium compounds such as osmium tetraoxide; (a6) ruthenium compounds such as ruthenium salts; (a7) vanadium compounds such as $VOCl_3$, $VOF_3$, $V_2O_5$, $NH_4VO_3$ and $NaVO_3$; (a8) thallium compounds such as thallium (III) acetate, trifluorothallium (III) acetate and thallium (III) nitrate; (a9) copper compounds such as copper (II) acetate, copper (II) trifluoromethane sulfonate, copper (II) trifluoroborate, copper (II) chloride and copper (I) acetate; (a10) iron compounds such as iron (III) chloride and potassium hexacyanoferrate (III); (a11) bismuth compounds such as sodium bismuthate; (a12) nickel compounds such as nickel peroxide, and the like.

Examples of the peroxides (b) include peracids such as peracetic acid and m-chloroperbenzoic acid; hydrogen peroxide, and hydroxyperoxides of such as alkylhydroxyperoxides such as t-butylhydroperoxide; diacyl peroxide, peracid esters, peracid ketal, peroxydicarbonate, dialkyl peroxide, peracid ketone, and the like.

Examples of the (c) diazotized compounds include 2,2'-azobisisobutyronitrile, and the like.

Examples of the halogen or halogen acid (d) include halogen selected from chlorine, bromine and iodine, perhalogen acid, halogen acid, halogenous acid, hypohalous acid and salts thereof, and the like. It is to be noted that halogen in the halogen acid is exemplified by chlorine, bromine and iodine. Also, specific examples of the halogen acid or salts thereof may include sodium perchlorate, sodium bromate, and the like.

Of these one-electron oxidants, the peroxides (b) and the diazotized compounds (c) are preferred, and particularly, m-chloroperbenzoic acid, t-butylhydroperoxide, and 2,2'-azobisisobutyronitrile are preferred. These are preferably used since metal residues and the like are less likely to be attached on the substrate.

It is to be noted that the accelerator (F) such as the one-electron oxidant may be used either alone, or two or more types of these may be used in combination.

The content of the accelerator (F) in the composition for forming a resist underlayer film is usually no greater than 1,000 parts by mass, preferably 0.01 to 500 parts by mass, and more preferably 0.1 to 100 parts by mass with respect to 100 parts by mass of the total amount of the compound (A) and the polymer (B).

<(G) Binder Resin>

As the binder resin (G), any of a variety of thermoplastic resins and thermosetting resins (other than the polymer (A2) and the polymer (B)) may be used. The thermoplastic resin is a component having an effect of providing the underlayer film with flow performances, mechanical characteristics, and the like of the thermoplastic resin added. Also, the thermosetting resin is a component that becomes insoluble in a solvent by curing with heat, thereby achieving an effect of inhibiting intermixing of the resultant resist underlayer film and the resist coating film formed thereon, and thus can be preferably used as the binder resin (G). Among the foregoings, thermosetting resins such as urea resins, melamine resins, and aromatic hydrocarbon resins are preferred. It should be noted that the binder resin (G) may be used either alone, or two or more types thereof may be used in combination.

The content of the binder resin (G) in the composition for forming a resist underlayer film is usually no greater than 20 parts by mass, and no greater than preferably 10 parts by mass with respect to 100 parts by mass of the total amount of the compound (A) and the polymer (B).

<(H) Radioactive Ray Absorbing Agent>

Examples of the radioactive ray absorbing agent (H) include dyes such as oil-soluble dyes, dispersion dyes, basic dyes, methine dyes, pyrazole dyes, imidazole dyes and hydroxyazo dyes; fluorescent whitening agents such as bixin derivatives, norbixin, stilbene, 4,4'-diaminostilbene derivatives, coumarin derivatives and pyrazoline derivatives; ultraviolet ray absorbing agents such as hydroxyazo dyes, as well as trade names "Tinuvin 234" and "Tinuvin 1130" (both manufactured by Ciba-Geigy Co.); aromatic compounds such as anthracene derivatives and anthraquinone derivatives, and the like. It is to be noted that the radioactive ray absorbing agent may be used either alone, or two or more thereof may be used as a mixture. The content of the radioactive ray absorbing agent is preferably no greater than 10 parts by mass, and more preferably no greater than 5 parts by mass with respect to 100 parts by mass of the total amount of the compound (A) and the polymer (B).

<(I) Surfactant>

The surfactant (I) is a component having an effect of improving the coating properties, striation, wettability, developability, and the like. The surfactant (I) may be used either alone, or two or more types thereof may be used in combination.

The content of the surfactant (I) in the composition for forming a resist underlayer film is usually no greater than 15 parts by mass, and no greater than preferably 10 parts by mass with respect to 100 parts by mass of the total amount of the compound (A) and the polymer (B).

As the binder resin (G), the radioactive ray absorbing agent (H) and the surfactant (I), for example, those disclosed in Japanese Unexamined Patent Application, Publication No. 2004-168748, and the like may be used.

Moreover, the resin composition for forming a resist underlayer film may contain, in addition to the components described above, for example, a storage stabilizer, a defoaming agent, an adhesion promoter, and the like.

<Method for Preparing the Composition for Forming a Resist Underlayer Film>

The composition for forming a resist underlayer film can be prepared by, for example, blending/mixing the compound (A), and as needed the polymer (B), the acid generator (D), the crosslinkable compound (E) and the other optional components, as well as the organic solvent (C), in general.

In the composition for forming a resist underlayer film, the solid content concentration, i.e., the total concentration of the components other than the organic solvent (C) with respect to the entirety of the composition is not particularly limited, but in light of the workability of the resist underlayer film form, the concentration is preferably 2 to 20% by mass, and more preferably 4 to 15% by mass.

<Composition for Forming a Resist Underlayer Film>

The composition for forming a resist underlayer film of the present invention is a composition for forming a resist underlayer film for use in a method for forming a pattern, the method including removing the resist underlayer film with an alkali liquid, and the composition for forming a resist underlayer film of the present invention contains the compound (A) having an alkali-cleavable functional group.

When the composition for forming a resist underlayer film is used in the method for forming a pattern in which the resist underlayer film is removed with the aforementioned alkali liquid, the resist underlayer film can be more easily removed with an alkali liquid while maintaining the etching resistance of the resist underlayer film formed, and consequently simplification of the pattern formation is enabled. In addition, according to the composition for forming a resist underlayer film, it is believed that the resist underlayer film pattern remaining on the substrate after the dry etching can be removed without an ashing treatment, and without need of application of energy by e.g., heating at a high temperature; therefore, a pattern having favorable qualities can be formed without influences such as deterioration, on the substrate having a pattern formed thereon.

With respect to the composition for forming a resist underlayer film, the explanation is omitted in this section since the method for forming a pattern in the above section already described in detail.

<Resist Underlayer Film>

The resist underlayer film is formed from the composition for forming a resist underlayer film. Since the resist underlayer film is formed from the composition for forming a resist underlayer film as described above, it can be more easily removed with an alkali liquid while maintaining the etching resistance.

EXAMPLES

Hereinafter, preferred modes for carrying out the present invention are explained in more detail by way of Examples, but the present invention is not anyhow limited to these Examples. Measurements of physical properties in the present Examples were carried out according to the methods described below.

[Weight Average Molecular Weight (Mw)]

The weight average molecular weight (Mw) of the polymer obtained was determined by gel permeation chromatography (detector: "differential refractometer") using "GPC column" (G2000HXL: two columns; and G3000HXL: one column) manufactured by Tosoh Corporation under an analytical condition including a flow rate of 1.0 mL/min and a column temperature of 40° C. with tetrahydrofuran as an elution solvent, using mono-dispersed polystyrene as a standard.

[$^1$H-NMR Analysis and $^{13}$C-NMR Analysis]

In $^1$H-NMR determination and $^{13}$C-NMR determination of the compound, a nuclear magnetic resonance apparatus ("JNM-ECX400P"; manufactured by JEOL, Ltd.) was used.

Synthesis of Compound (A)

Synthesis Example 1

Synthesis of Compound (A-1)

In a reaction apparatus equipped with a thermometer and a stirrer were charged 2.96 g of 1-hydroxy-2,3-epoxypropane, 12.18 g of 1,8-diazabicyclo[5.4.0]undeca-7-ene, and 30 g of tetrahydrofuran in a nitrogen atmosphere. Thereto was added dropwise a solution prepared by dissolving 3.80 g of chloroacetic acid in 10 g of tetrahydrofuran while cooling the reaction apparatus on ice. The reaction was allowed for 5 hrs, and the organic layer was separated from the water layer. To this organic layer were added 8.25 g of N,N'-dicyclohexyl carbodiimide, and 0.30 g of N,N'-dimethylaminopyridine. Thereto was added dropwise a solution prepared by adding 2.20 g of 1,4-dihydroxybenzene to 10 g of tetrahydrofuran and permitting dissolution while cooling on ice. After the reaction was allowed for 3 hrs, the organic layer was separated from the water layer to obtain 4.87 g of a compound (compound (A-1)) having a structure represented by the following formula (A-1):

[chemical formula 20]

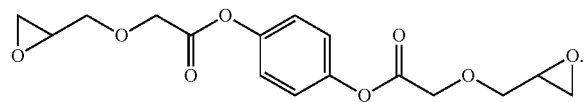

(A-1)

The NMR data for the determination of the compound (A-1) obtained are as follows:

$^1$H-NMR (solvent: CDCl$_3$) δ (ppm): 7.23 (s, 4H), 4.31 (m, 4H), 3.38-3.63 (m, 4H), 2.86 (m, 2H), 2.38-2.63 (m, 4H); and $^{13}$C-NMR (solvent: CDCl$_3$) δ (ppm): 166.0, 148.1, 122.0, 73.2, 67.0, 55.2, 44.2.

Synthesis of Polymer (B)

Synthesis Example 2

Synthesis of Polymer (B-1)

In a reaction apparatus equipped with a capacitor, a thermometer and a stirring device were charged 100 parts by mass of 2,7-dihydroxynaphthalene, 200 parts by mass of propylene glycol monomethyl ether acetate and 50 parts by mass of paraformaldehyde, and thereto were added 2 parts by mass of oxalic acid. The temperature was elevated to 120° C. while permitting dehydration, and the reaction was allowed for 5 hrs to obtain a polymer (B-1). The resulting polymer had a Mw of 2,000, with a yield of 80%.

Synthesis Example 3

Synthesis of Polymer (B-2)

In a separable flask equipped with a thermometer were charged 70 parts by mass of acenaphthylene, 20 parts by mass of hydroxyethyl methacrylate and 10 parts by mass of styrene as monomers, 10 parts by mass of 2,2'-azobis(dimethyl 2-methylbutyrate) (manufactured by Wako Pure Chemical Industries, Ltd., trade name "V-601") as a radical polymerization initiator, and 400 parts by mass of methyl isobutyl ketone as a solvent in a nitrogen atmosphere. Then, polymerization was carried out at 90° C. for 4 hrs while stirring the mixture. After completing the polymerization, the polymerization solution was cooled with to no greater than 30° C. After cooling, the polymerization solution was charged into a large quantity of methanol to precipitate a white solid. Thereafter, the precipitated white solid was separated by a decantation process, and the white solid separated was washed with a large quantity of methanol, followed by drying at 50° C. for 17 hrs to obtain a polymer (B-2). The resulting polymer had a Mw of 4,000, with a yield of 75%.

Synthesis Example 4

Synthesis of Polymer (B-3)

In a reaction apparatus equipped with a capacitor, a thermometer and a stirring device were charged 100 parts by mass of 9,9-bis(4-hydroxyphenyl)fluorene, 100 parts by mass of propylene glycol monomethyl ether acetate and 50 parts by mass of paraformaldehyde, and thereto were added 2 parts by mass of oxalic acid. The temperature was elevated to 120° C. while permitting dehydration, and the reaction was allowed for 5 hrs to obtain a polymer (B-3) constituted with a structure unit represented by the following formula (B-3). The resulting polymer had a Mw of 4,000, with a yield of 82%.

[chemical formula 21]

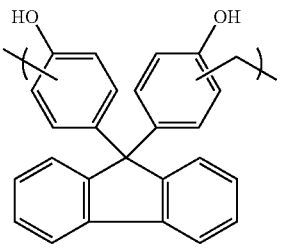

(B-3)

<Preparation of Composition for Forming a Resist Underlayer Film>

Components (the organic solvent (C) and the acid generating agent (D)) other than the compound (A-1) and the polymers (B-1) to (B-3) constituting the composition for forming a resist underlayer film obtained in the above Synthesis Examples are shown below.

(C) Organic Solvent (C-1) Propylene Glycol Monomethyl Ether Acetate (D) Acid Generating Agent (D-1) Diphenyliodonium Trifluoromethane Sulfonate Example 1

The compound (A-1) in an amount of 1 part by mass, 10 parts by mass of the polymer (B-1) and 90 parts by mass of the organic solvent (C-1), and 0.1 parts by mass were mixed to permit dissolution. The resulting solution was filtered through a membrane filter having a pore size of 0.1 μm, whereby a composition for forming a resist underlayer film of Example 1 was prepared.

Example 2

A composition for forming a resist underlayer film of Example 2 was prepared in a similar manner to Example 1 except that the polymer (B-2) was used in Example 1 in place of the polymer (B-1) as the polymer (B).

Example 3

A composition for forming a resist underlayer film of Example 3 was prepared in a similar manner to Example 1 except that the polymer (B-3) was used in Example 1 in place of the polymer (B-1) as the polymer (B).

Synthesis Example 5

A composition for forming a resist underlayer film of Synthesis Example 5 was prepared in a similar manner to Example 1 except that 1 part by mass of 1,3,4,6-tetrakis (methoxymethyl)glycoluril (i.e., a compound represented by the following formula (a-1)) was used in Example 1 in place of 1 part by mass of the compound (A-1).

[chemical formula 22]

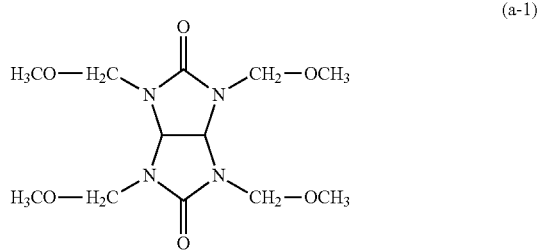

(a-1)

Synthesis Example 6

A composition for forming a resist underlayer film of Synthesis Example 6 was prepared in a similar manner to Synthesis Example 5 except that the polymer (B-2) was used in Synthesis Example 5 in place of the polymer (B-1) as the polymer (B).

Formation of Pattern

Example 4

After a coating film was obtained on a 12 inch silicon wafer as a substrate by spin coating the composition for forming a resist underlayer film of Example 1, post baking (PB) was carried out at 250° C. for 60 sec, followed by cooling at 23° C. for 30 sec to form a resist underlayer film having a film thickness of 100 nm. On this resist underlayer film, an intermediate layer composition for a three layer resist process was spin coated, and subjected to PB at 220° C. for 60 sec, followed by cooling at 23° C. for 30 sec to form a resist intermediate layer film having a film thickness of 40 nm. Next, a resist composition ("ARF AR2772JN", manufactured by JSR Corporation) was spin coated on the resist intermediate layer film, and subjected to PB at 100° C. for 60 sec, followed by cooling at 23° C. for 30 sec to form a resist coating film having a film thickness of 100 nm. Furthermore, an upper layer film form composition was spin-coated on the coating film formed using a coater/developer ("Lithius Pro-i", manufactured by Tokyo Electron Limited), followed by PB carried out at 90° C. for 60 sec to form an upper layer film having a film thickness of 90 nm.

Subsequently, exposure was carried out through a photomask for formation of 42 nm line/84 nm pitch using an ArF Immersion Scanner ("S610C", manufactured by NIKON) under an optical condition of dipole with NA of 1.30. Post exposure baking (PEB) was carried out on a hot plate of the aforementioned coater/developer at 100° C. for 60 sec, followed by cooling at 23° C. for 30 sec. Thereafter, paddle development was carried out for 30 sec with an LD nozzle of a cup for development using an aqueous tetramethylammonium hydroxide (TMAH) solution as a developer, followed by rinsing with ultra pure water. Thereafter, a resist pattern of 42 nm line/84 nm pitch was formed by spin-drying through swinging off at 2,000 rpm for 15 sec.

Furthermore, the wafer having the resist pattern thus formed was subjected to etching so as to transfer the resist pattern to the resist intermediate layer film using a dry etching apparatus ("TE-8500P", manufactured by Tokyo Electron Limited) with $CHF_3/CF_4/Ar$ (chamber pressure: 40.0 Pa; RF power: 500 W; gap: 9 mm; $CHF_3$ gas flow rate: 20 mL/min; $CF_4$ gas flow rate: 60 mL/min; Ar gas flow rate: 200 mL/min; time: 30 sec). The pattern was further transferred from the resist intermediate layer film to the resist underlayer film situated below the resist intermediate layer film with $Ar/O_2$ (chamber pressure: 60.0 Pa; RF power: 300 W; Ar gas flow rate: 40 mL/min; $O_2$ gas flow rate: 60 mL/min; gap: 9 mm; time: 20 sec). Then the resist underlayer film was subjected to etching processing with $CHF_3/CF_4/Ar$ (chamber pressure: 40.0 Pa; RF power: 500 W; gap: 9 mm; $CHF_3$ gas flow rate: 20 mL/min; $CF_4$ gas flow rate: 60 mL/min; Ar gas flow rate: 200 mL/min; time: 30 sec) whereby the pattern was transferred to the silicon wafer.

In addition, for the purpose of removing a residual film of the underlayer film used as a mask in transferring to the silicon wafer, the silicon wafer was immersed in a 10% by mass aqueous TMAH solution at 50° C. for 10 min, and thereafter in 2-propanol for 10 min, followed by washing with water and drying to form a pattern of Example 3.

Examples 5 and 6, and Comparative Examples 1 and 2

Each pattern of Examples 5 and 6, and Comparative Examples 1 and 2 was formed in a similar manner to Example 4 except that the composition for forming a resist underlayer film of Example 2 or 3 or Synthesis Example 5 or 6 was used in Example 4 in place of the composition for forming a resist underlayer film of Example 1.

<Evaluation>

The methods for forming a pattern of the aforementioned Examples and Comparative Examples were evaluated on removability with an alkali liquid and etching resistance of the resist underlayer film formed according to the following methods.

[Removability with Alkali Liquid]

On a silicon wafer having a diameter of 8 inch, each of the compositions for forming a resist underlayer film of the aforementioned Examples and Comparative Examples was spin coated, and then heated on a hot plate at 350° C. for 120 sec to form a resist underlayer film having a film thickness of 300 nm. The resulting underlayer film was immersed in a 10% by mass aqueous TMAH solution at 50° C. for 10 min, and immersed in 2-propanol for 10 min, followed by washing with water and drying. The film thickness of the underlayer film on this silicon wafer was measured, whereas the film thickness of the residual underlayer film was measured using a film thickness measurement equipment (manufactured by KLA Tencor, "UV1280SE"). The removability with the alkali liquid of the resist underlayer film was evaluated according to the following criteria. The results of evaluation are shown in Table 1.

"A": the film thickness of the residual film of the resist underlayer film being less than 5 nm; and "B": the film thickness of the residual film of the resist underlayer film being no less than 5 nm.

[Etching Resistance]

On a silicon wafer having a diameter of 8 inch, each of the compositions for forming a resist underlayer film of the aforementioned Examples and Comparative Examples was spin coated, and then heated on a hot plate having an oxygen concentration of 20% by volume at 180° C. for 60 sec, and subsequently at 350° C. for 120 sec to form a resist underlayer film having a film thickness of 0.3 μm. This resist underlayer film was subjected to an etching process using an etching apparatus "EXAM" (manufactured by SHINKO SEIKI Co. Ltd.), with $CF_4/Ar/O_2$ ($CF_4$: 40 mL/min, Ar: 20 mL/min, $O_2$: 5 mL/min, pressure: 20 Pa; RF power: 200 W; process time: 40 sec; temperature: 15° C.)

Thereafter, the etching rate was determined by measuring the film thicknesses before and after the etching process.

As a result, each of the compositions for forming a resist underlayer film of Examples 1 to 3 and Comparative Examples 1 and 2 exhibited an etching rate of no greater than 150 nm/min, and thus it was verified that formation of a resist underlayer film having etching resistance that was satisfactory for practical applications was enabled.

As shown in Examples in Table 1, it was indicated that the resist underlayer film formed from the composition for forming a resist underlayer film containing a compound (A) having an alkali-cleavable functional group was able to be easily removed with an alkali liquid. On the other hand, as demonstrated by Comparative Examples, it was difficult to remove the resist underlayer film formed from the composition for forming a resist underlayer film in which a crosslinkable compound not having an alkali-cleavable functional group was used, even if treated with an alkali liquid, as the resist underlayer film remained.

INDUSTRIAL APPLICABILITY

The composition for forming a resist underlayer film of the present invention is suitable as a material for forming an underlayer film used in multilayer resist processes that are suited for microfabrication in lithography processes, particularly in production of highly integrated circuit elements.

What is claimed is:

1. A composition for forming a resist underlayer film for use in a method for forming a pattern, comprising:
the resist underlayer film being capable of being removed with an alkali liquid,
the composition comprising a compound having an alkali-cleavable functional group, and
the alkali-cleavable functional group having a structure that generates a polar group by cleavage in an alkaline aqueous solution,
wherein the compound having an alkali-cleavable functional group has crosslinkability and is represented by the following formula (1):

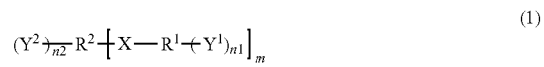

(1)

wherein, $Y^1$ and $Y^2$ each independently represent a crosslinkable functional group; X represents an alkali-cleavable functional group; $R^1$ represents a linking group having a valency of (n1+1); $R^2$ represents a linking group having a valency of (n2+m); n1 is an integer of 1 to 3; n2 is an integer of 0 to 3; m is an integer of 1 to 3; wherein, n1, m and n2 satisfy the formula of: (n1×m+n2)≥2, and provided that $Y^1$, $Y^2$, X and $R^1$ are each present in plural number, the $Y^1$, $Y^2$, X and $R^1$ present in plural number may be each the same or different.

TABLE 1

| Composition for forming a resist underlayer film | Method for forming a pattern | [A] Component | | [B] Polymer | | [C] Organic solvent | | [D] Acid generating agent | | Evaluation Removability with alkali liquid |
|---|---|---|---|---|---|---|---|---|---|---|
| | | type | amount (parts by mass) | type | amount (parts by mass) | type | amount (parts by mass) | type | amount (parts by mass) | |
| Example 1 | Example 4 | A-1 | 1 | B-1 | 10 | C-1 | 90 | D-1 | 0.1 | A |
| Example 2 | Example 5 | A-1 | 1 | B-2 | 10 | C-1 | 90 | D-1 | 0.1 | A |
| Example 3 | Example 6 | A-1 | 1 | B-3 | 10 | C-1 | 90 | D-1 | 0.1 | A |
| Synthesis Example 5 | Comparative Example 1 | a-1 | 1 | B-1 | 10 | C-1 | 90 | D-1 | 0.1 | B |
| Synthesis Example 6 | Comparative Example 2 | a-1 | 1 | B-2 | 10 | C-1 | 90 | D-1 | 0.1 | B |

2. The composition for forming a resist underlayer film according to claim 1, wherein the compound represented by the above formula (1) is represented by the following formula (1-1) or (1-2):

$$Y^{11}-R^{11}-X^1-R^{20}-X^2-R^{12}-Y^{12} \qquad (1\text{-}1)$$

$$Y^{2'}-R^{20'}-X'-R^{1'}-Y^{1'} \qquad (1\text{-}2)$$

wherein, $Y^{11}$, $Y^{12}$, $Y^{1'}$ and $Y^{2'}$ each independently represent a monovalent group each represented by one of the following formulae (Y1) to (Y4):

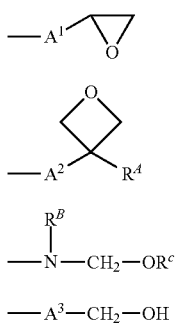

in the formulae (Y1) to (Y4), $A^1$ and $A^2$ each independently represent a single bond, an alkanediyl group having 1 to 4 carbon atoms or an oxyalkanediyl group; $A^3$ represents a bivalent aromatic hydrocarbon group; $R^A$ represents an alkyl group having 1 to 4 carbon atoms; $R^B$ represents a hydrogen atom or an alkyl group having 1 to 6 carbon atoms; and $R^C$ represents an alkyl group having 1 to 4 carbon atoms;

$X^1$, $X^2$ and $X'$ represent an ester group; $R^{11}$, $R^{12}$, $R^{1'}$, $R^{20}$ and $R^{20'}$ each independently represent a phenylene group, a naphthylene group, an isopropylidenediphenylene group or an alkanediyl group having 1 to 6 carbon atoms which is unsubstituted or substituted with a fluorine atom, wherein a part or all of hydrogen atoms of the aromatic ring of the phenylene group, the naphthylene group and the isopropylidenediphenylene group are unsubstituted or substituted by an alkyl group, a cycloalkyl group, an aryl group, a halogen atom, a hydroxyl group, a cyano group or an amino group.

3. The composition for forming a resist underlayer film according to claim 1, wherein a content of the compound having an alkali-cleavable functional group in the composition is from 1% by mass to 50% by mass with respect to a solid content of the composition.

4. The composition for forming a resist underlayer film according to claim 1, wherein the composition further comprises a polymer not having an alkali-cleavable functional group.

5. The composition for forming a resist underlayer film according to claim 4, wherein the polymer comprises a structural unit comprising an aromatic group or an alicyclic group.

6. The composition for forming a resist underlayer film according to claim 5, wherein the structural unit comprises a structure unit derived from at least one hydrocarbon selected from the group consisting of acenaphthylene, naphthalene, fluorene, indene and nortricyclene.

7. The composition for forming a resist underlayer film according to claim 4, wherein a content of the compound having an alkali-cleavable functional group with respect to 100 parts by mass of the polymer is no less than 5 parts by mass.

8. The composition for forming a resist underlayer film according to claim 4, wherein a content of the polymer is the no less than 10% by mass with respect a solid content of the composition.

9. The composition for forming a resist underlayer film according to claim 1, wherein the composition further comprises an organic solvent.

10. The composition for forming a resist underlayer film according to claim 1, wherein the composition further comprises an acid generator.

11. The composition for forming a resist underlayer film according to claim 1, wherein the composition further comprises a crosslinkable compound other than the compound having an alkali-cleavable functional group.

* * * * *